(12) United States Patent
Ross

(10) Patent No.: US 11,872,159 B2
(45) Date of Patent: Jan. 16, 2024

(54) PRE-ALIGNMENT SURGICAL CASSETTE INTERFACE

(71) Applicant: JOHNSON & JOHNSON SURGICAL VISION, INC., Irvine, CA (US)

(72) Inventor: Mark W. Ross, Costa Mesa, CA (US)

(73) Assignee: Johnson & Johnson Surgical Vision, Inc., Irvine, CA (US)

(*) Notice: Subject to any disclaimer, the term of this patent is extended or adjusted under 35 U.S.C. 154(b) by 66 days.

(21) Appl. No.: 16/389,657

(22) Filed: Apr. 19, 2019

(65) Prior Publication Data
US 2019/0307607 A1 Oct. 10, 2019

Related U.S. Application Data

(60) Division of application No. 13/944,726, filed on Jul. 17, 2013, now Pat. No. 10,265,217, which is a
(Continued)

(51) Int. Cl.
*A61F 9/007* (2006.01)
*A61F 9/008* (2006.01)
(Continued)

(52) U.S. Cl.
CPC .......... *A61F 9/00736* (2013.01); *A47B 81/00* (2013.01); *A61B 3/16* (2013.01);
(Continued)

(58) Field of Classification Search
CPC .......... A61M 2205/12; A61M 2205/14; A61M 2205/3569; A61M 2210/0612;
(Continued)

(56) References Cited

U.S. PATENT DOCUMENTS 1,848,024 A   3/1932  Owen
2,123,781 A   7/1938  Huber
(Continued)

FOREIGN PATENT DOCUMENTS

AU    2006235983 A1   5/2007
DE       3826414 A1   2/1989
(Continued)

OTHER PUBLICATIONS

European Search Report for Application No. EP16199518, dated Mar. 22, 2017, 9 pages.
(Continued)

*Primary Examiner* — Scott J Medway
(74) *Attorney, Agent, or Firm* — Johnson & Johnson Surgical Vision, Inc.

(57) ABSTRACT

A phacoemulsification surgical console, and a related system and method. The console, system and method may include a cassette receiver suitable for receiving a surgical cassette, a controller suitable for controlling provided aspects of the phacoemulsification; and a pre-alignment feature along a lower portion under and proximate to the cassette receiver, extending outwardly from the lower portion, and suitable for aligning the surgical cassette to the cassette receiver. The pre-alignment feature may comprise a shelf.

7 Claims, 23 Drawing Sheets

Related U.S. Application Data continuation-in-part of application No. 13/776,988, filed on Feb. 26, 2013, now Pat. No. 9,700,457.

(60) Provisional application No. 61/612,307, filed on Mar. 17, 2012.

(51) Int. Cl.
  *A61M 3/02* (2006.01)
  *A61M 1/00* (2006.01)
  *A61B 3/16* (2006.01)
  *A47B 81/00* (2006.01)

(52) U.S. Cl.
  CPC .............. *A61F 9/007* (2013.01); *A61F 9/008* (2013.01); *A61F 9/00745* (2013.01); *A61M 1/71* (2021.05); *A61M 1/72* (2021.05); *A61M 1/77* (2021.05); *A61M 3/0201* (2021.05); *A61M 3/022* (2014.02); *A61M 3/0216* (2014.02); *A61M 1/73* (2021.05); *A61M 1/74* (2021.05); *A61M 1/774* (2021.05); *A61M 3/0202* (2021.05); *A61M 3/0258* (2013.01); *A61M 2205/12* (2013.01); *A61M 2205/121* (2013.01); *A61M 2205/123* (2013.01); *A61M 2205/128* (2013.01); *A61M 2205/3331* (2013.01); *A61M 2205/3379* (2013.01); *A61M 2205/505* (2013.01); *A61M 2210/0612* (2013.01); *Y10T 29/49826* (2015.01)

(58) Field of Classification Search
  CPC .......... A61M 2205/121; A61M 1/0031; A61M 1/0058; A61F 9/00736; A61F 9/00745; A61F 9/007
  See application file for complete search history.

(56) References Cited

U.S. PATENT DOCUMENTS

| | | | |
|---|---|---|---|
| 2,990,616 A | 7/1961 | Balamuth et al. | |
| 3,076,904 A | 2/1963 | Claus et al. | |
| 3,116,697 A | 1/1964 | Theodore | |
| 3,439,680 A | 4/1969 | Thomas, Jr. | |
| 3,526,218 A | 9/1970 | Robert et al. | |
| 3,526,219 A | 9/1970 | Lewis | |
| 3,781,142 A | 12/1973 | Zweig | |
| 3,857,387 A | 12/1974 | Shock | |
| 3,900,170 A * | 8/1975 | Serizawa | G11B 15/67565 |
| 3,980,255 A * | 9/1976 | Serizawa | G11B 23/08735 |
| 4,017,828 A | 4/1977 | Watanabe et al. | |
| 4,037,491 A | 7/1977 | Newbold | |
| 4,189,286 A | 2/1980 | Murry et al. | |
| 4,193,004 A | 3/1980 | Lobdell et al. | |
| 4,247,784 A | 1/1981 | Henry | |
| 4,276,023 A | 6/1981 | Phillips et al. | |
| 4,286,464 A | 9/1981 | Tauber et al. | |
| 4,479,760 A * | 10/1984 | Bilstad | A61M 1/3496 128/DIG. 12 |
| 4,537,561 A | 8/1985 | Xanthopoulos | |
| 4,564,342 A | 1/1986 | Weber et al. | |
| 4,590,934 A | 5/1986 | Malis et al. | |
| 4,662,829 A | 5/1987 | Nehring | |
| 4,665,621 A | 5/1987 | Ackerman et al. | |
| 4,706,687 A | 11/1987 | Rogers et al. | |
| 4,713,051 A * | 12/1987 | Steppe | A61F 9/00736 604/35 |
| 4,735,558 A | 4/1988 | Kienholz et al. | |
| 4,757,814 A | 7/1988 | Wang et al. | |
| 4,758,220 A | 7/1988 | Sundblom et al. | |
| 4,758,238 A * | 7/1988 | Sundblom | A61M 1/0001 604/153 |
| 4,772,263 A | 9/1988 | Dorman et al. | |
| 4,773,897 A | 9/1988 | Scheller et al. | |
| 4,798,580 A * | 1/1989 | DeMeo | A61M 1/0058 604/30 |
| 4,818,186 A | 4/1989 | Pastrone et al. | |
| 4,819,317 A | 4/1989 | Bauer et al. | |
| 4,837,857 A | 6/1989 | Scheller et al. | |
| 4,920,336 A | 4/1990 | Meijer | |
| 4,920,645 A | 5/1990 | Baudouin | |
| 4,921,477 A | 5/1990 | Davis | |
| 4,925,444 A | 5/1990 | Orkin et al. | |
| 4,933,843 A | 6/1990 | Scheller et al. | |
| 4,933,943 A | 6/1990 | Narhi et al. | |
| 4,941,518 A | 7/1990 | Williams et al. | |
| 4,954,960 A | 9/1990 | Lo et al. | |
| 4,961,424 A | 10/1990 | Kubota et al. | |
| 4,963,131 A * | 10/1990 | Wortrich | A61M 1/0058 604/250 |
| 4,965,417 A | 10/1990 | Massie | |
| 4,983,901 A | 1/1991 | Lehmer | |
| 4,998,972 A | 3/1991 | Chin et al. | |
| 5,006,110 A | 4/1991 | Garrison et al. | |
| 5,020,535 A | 6/1991 | Parker et al. | |
| 5,026,387 A | 6/1991 | Thomas | |
| 5,032,939 A | 7/1991 | Mihara et al. | |
| 5,039,973 A | 8/1991 | Carballo | |
| 5,091,656 A | 2/1992 | Gahn | |
| 5,106,366 A * | 4/1992 | Steppe | A61M 1/0058 417/477.2 |
| 5,108,367 A | 4/1992 | Epstein et al. | |
| 5,110,270 A | 5/1992 | Morrick | |
| 5,125,891 A | 6/1992 | Hossain et al. | |
| 5,160,317 A | 11/1992 | Costin | |
| 5,195,960 A | 3/1993 | Hossain et al. | |
| 5,195,961 A | 3/1993 | Takahashi et al. | |
| 5,195,971 A | 3/1993 | Sirhan | |
| 5,230,614 A | 7/1993 | Zanger et al. | |
| 5,242,404 A | 9/1993 | Conley et al. | |
| 5,249,121 A | 9/1993 | Baum et al. | |
| 5,268,624 A | 12/1993 | Zanger | |
| 5,271,379 A | 12/1993 | Phan et al. | |
| 5,273,517 A * | 12/1993 | Barone | A61M 1/3621 251/5 |
| 5,282,787 A | 2/1994 | Wortrich | |
| 5,323,543 A | 6/1994 | Steen et al. | |
| 5,342,293 A | 8/1994 | Zanger | |
| 5,350,357 A | 9/1994 | Kamen et al. | |
| 5,351,676 A | 10/1994 | Putman | |
| 5,354,268 A | 10/1994 | Peterson et al. | |
| 5,364,144 A | 11/1994 | Satterfield et al. | |
| 5,388,569 A | 2/1995 | Kepley | |
| 5,445,506 A * | 8/1995 | Afflerbaugh | F04B 43/1253 417/477.2 |
| 5,454,783 A | 10/1995 | Grieshaber et al. | |
| 5,460,490 A * | 10/1995 | Carr | A61M 1/0058 417/44.2 |
| 5,464,391 A | 11/1995 | DeVale | |
| 5,470,211 A | 11/1995 | Knott et al. | |
| 5,470,312 A | 11/1995 | Zanger et al. | |
| 5,499,969 A | 3/1996 | Beuchat et al. | |
| 5,505,330 A | 4/1996 | Nunes | |
| 5,520,652 A | 5/1996 | Peterson | |
| 5,531,697 A | 7/1996 | Olsen et al. | |
| 5,533,976 A | 7/1996 | Zaleski et al. | |
| 5,549,461 A | 8/1996 | Newland | |
| 5,554,894 A | 9/1996 | Sepielli | |
| 5,558,240 A | 9/1996 | Karp | |
| 5,561,575 A | 10/1996 | Eways | |
| 5,569,188 A | 10/1996 | Mackool | |
| 5,580,347 A | 12/1996 | Reimels | |
| 5,591,127 A | 1/1997 | Barwick et al. | |
| 5,653,887 A | 8/1997 | Wahl et al. | |
| 5,657,000 A | 8/1997 | Ellingboe | |
| 5,676,530 A * | 10/1997 | Nazarifar | A61M 1/77 417/477.2 |
| 5,676,649 A | 10/1997 | Boukhny et al. | |
| 5,676,650 A | 10/1997 | Grieshaber et al. | |
| 5,693,020 A | 12/1997 | Rauh | |
| 5,697,898 A | 12/1997 | Devine | |
| 5,697,910 A | 12/1997 | Cole et al. | |
| 5,700,240 A | 12/1997 | Barwick, Jr. et al. | |

(56) References Cited

U.S. PATENT DOCUMENTS

| | | | |
|---|---|---|---|
| 5,702,357 A * | 12/1997 | Bainbridge | A61M 1/30 604/4.01 |
| 5,724,264 A | 3/1998 | Rosenberg et al. | |
| 5,728,130 A | 3/1998 | Ishikawa et al. | |
| 5,733,256 A | 3/1998 | Costin | |
| 5,745,647 A | 4/1998 | Krause | |
| 5,746,713 A | 5/1998 | Hood et al. | |
| 5,747,824 A | 5/1998 | Jung et al. | |
| 5,752,918 A | 5/1998 | Fowler et al. | |
| 5,777,602 A | 7/1998 | Schaller et al. | |
| 5,805,998 A | 9/1998 | Kodama | |
| 5,807,075 A | 9/1998 | Jacobsen et al. | |
| 5,810,766 A | 9/1998 | Barnitz et al. | |
| 5,830,176 A | 11/1998 | Mackool | |
| 5,843,109 A | 12/1998 | Mehta et al. | |
| 5,859,642 A | 1/1999 | Jones | |
| 5,871,492 A | 2/1999 | Sorensen | |
| 5,879,298 A | 3/1999 | Drobnitzky et al. | |
| 5,883,615 A | 3/1999 | Fago et al. | |
| 5,899,674 A | 5/1999 | Jung et al. | |
| 5,910,110 A * | 6/1999 | Bastable | A61F 9/00736 600/398 |
| 5,928,257 A | 7/1999 | Kablik et al. | |
| 5,938,655 A | 8/1999 | Bisch et al. | |
| 5,983,749 A | 11/1999 | Holtorf | |
| 6,002,484 A | 12/1999 | Rozema et al. | |
| 6,024,428 A | 2/2000 | Uchikata | |
| 6,028,387 A | 2/2000 | Boukhny | |
| D423,349 S | 4/2000 | Lyons et al. | |
| 6,062,829 A | 5/2000 | Ognier | |
| 6,070,761 A * | 6/2000 | Bloom | A61J 3/002 141/330 |
| 6,077,285 A | 6/2000 | Boukhny | |
| 6,086,598 A | 7/2000 | Appelbaum et al. | |
| 6,109,895 A | 8/2000 | Ray et al. | |
| 6,117,126 A | 9/2000 | Appelbaum et al. | |
| 6,129,656 A * | 10/2000 | Blakeslee | A61M 1/3696 494/45 |
| 6,139,320 A | 10/2000 | Hahn | |
| 6,150,623 A | 11/2000 | Chen | |
| 6,159,175 A | 12/2000 | Strukel et al. | |
| 6,179,829 B1 | 1/2001 | Bisch et al. | |
| 6,200,287 B1 | 3/2001 | Keller et al. | |
| 6,219,032 B1 | 4/2001 | Rosenberg et al. | |
| 6,251,113 B1 | 6/2001 | Appelbaum et al. | |
| 6,260,434 B1 | 7/2001 | Holtorf | |
| 6,360,630 B2 | 3/2002 | Holtorf | |
| 6,368,269 B1 | 4/2002 | Lane | |
| 6,383,804 B1 | 5/2002 | Ward, Jr. et al. | |
| 6,411,062 B1 | 6/2002 | Baranowski et al. | |
| 6,424,124 B2 | 7/2002 | Ichihara et al. | |
| 6,436,072 B1 | 8/2002 | Kullas et al. | |
| 6,452,120 B1 | 9/2002 | Chen | |
| 6,452,123 B1 | 9/2002 | Chen | |
| 6,491,661 B1 | 12/2002 | Boukhny et al. | |
| 6,511,454 B1 | 1/2003 | Nakao et al. | |
| 6,537,445 B2 | 3/2003 | Muller | |
| 6,595,948 B2 | 7/2003 | Suzuki et al. | |
| 6,632,214 B2 | 10/2003 | Morgan et al. | |
| 6,674,030 B2 | 1/2004 | Chen et al. | |
| 6,780,166 B2 | 8/2004 | Kanda et al. | |
| 6,830,555 B2 | 12/2004 | Rockley et al. | |
| 6,852,092 B2 | 2/2005 | Kadziauskas et al. | |
| 6,862,951 B2 | 3/2005 | Peterson et al. | |
| 6,908,451 B2 | 6/2005 | Brody et al. | |
| 6,962,488 B2 | 11/2005 | Davis et al. | |
| 6,962,581 B2 | 11/2005 | Thoe | |
| 6,986,753 B2 | 1/2006 | Bui | |
| 7,011,761 B2 | 3/2006 | Muller | |
| 7,012,203 B2 | 3/2006 | Hanson et al. | |
| 7,070,578 B2 | 7/2006 | Leukanech et al. | |
| 7,073,083 B2 | 7/2006 | Litwin, Jr. et al. | |
| 7,087,049 B2 | 8/2006 | Nowlin et al. | |
| 7,103,344 B2 | 9/2006 | Menard | |
| 7,167,723 B2 | 1/2007 | Zhang | |
| 7,168,930 B2 | 1/2007 | Cull et al. | |
| 7,169,123 B2 | 1/2007 | Kadziauskas et al. | |
| 7,236,766 B2 | 6/2007 | Freeburg | |
| 7,236,809 B2 | 6/2007 | Fischedick et al. | |
| 7,238,010 B2 * | 7/2007 | Hershberger | F04B 43/1253 417/477.2 |
| 7,242,765 B2 | 7/2007 | Hairston | |
| 7,244,240 B2 | 7/2007 | Nazarifar et al. | |
| 7,289,825 B2 | 10/2007 | Fors et al. | |
| 7,300,264 B2 | 11/2007 | Souza | |
| 7,316,664 B2 | 1/2008 | Kadziauskas et al. | |
| 7,336,976 B2 | 2/2008 | To | |
| 7,381,917 B2 | 6/2008 | Dacquay et al. | |
| 7,439,463 B2 | 10/2008 | Brenner et al. | |
| 7,465,285 B2 | 12/2008 | Hutchinson et al. | |
| 7,470,277 B2 | 12/2008 | Finlay et al. | |
| 7,479,123 B2 * | 1/2009 | Briggs | A61K 41/0066 604/6.08 |
| 7,526,038 B2 | 4/2009 | McNamara | |
| 7,591,639 B2 | 9/2009 | Kent | |
| 7,731,484 B2 | 6/2010 | Yamamoto et al. | |
| 7,776,006 B2 | 8/2010 | Childers et al. | |
| 7,785,316 B2 | 8/2010 | Claus et al. | |
| 7,811,255 B2 | 10/2010 | Boukhny et al. | |
| 7,883,521 B2 | 2/2011 | Rockley et al. | |
| 7,921,017 B2 | 4/2011 | Claus et al. | |
| 7,935,074 B2 * | 5/2011 | Plahey | A61M 1/281 604/29 |
| 7,967,777 B2 | 6/2011 | Edwards et al. | |
| 8,057,679 B2 * | 11/2011 | Yu | A61M 1/281 700/273 |
| 8,070,712 B2 | 12/2011 | Muri et al. | |
| 8,075,468 B2 | 12/2011 | Min et al. | |
| 8,114,276 B2 * | 2/2012 | Childers | A61M 1/3649 417/474 |
| D693,463 S | 11/2013 | Burger et al. | |
| D698,019 S | 1/2014 | Oliveira | |
| 9,033,940 B2 | 5/2015 | Muri et al. | |
| 9,386,922 B2 | 7/2016 | Ross et al. | |
| 9,561,001 B2 * | 2/2017 | Keenan | A61B 5/157 |
| 9,561,323 B2 * | 2/2017 | Plahey | A61M 1/28 |
| 9,877,865 B2 | 1/2018 | Links | |
| 9,895,262 B2 | 2/2018 | Ross et al. | |
| 10,441,461 B2 | 10/2019 | Muri et al. | |
| 10,583,040 B2 | 3/2020 | Ross et al. | |
| 2001/0047166 A1 | 11/2001 | Wuchinich | |
| 2001/0051788 A1 | 12/2001 | Paukovits et al. | |
| 2002/0019215 A1 | 2/2002 | Romans | |
| 2002/0045887 A1 | 4/2002 | Dehoogh et al. | |
| 2002/0070840 A1 | 6/2002 | Fischer et al. | |
| 2002/0098859 A1 | 7/2002 | Murata | |
| 2002/0137007 A1 | 9/2002 | Beerstecher | |
| 2002/0179462 A1 | 12/2002 | Silvers | |
| 2002/0183693 A1 | 12/2002 | Peterson et al. | |
| 2003/0028091 A1 | 2/2003 | Simon et al. | |
| 2003/0050619 A1 | 3/2003 | Mooijman et al. | |
| 2003/0083016 A1 | 5/2003 | Evans et al. | |
| 2003/0106861 A1 * | 6/2003 | Gibbs | A61M 1/30 210/806 |
| 2003/0108429 A1 | 6/2003 | Angelini et al. | |
| 2003/0125717 A1 | 7/2003 | Whitman | |
| 2003/0202894 A1 * | 10/2003 | Leukanech | A61M 1/0058 417/477.2 |
| 2003/0224729 A1 | 12/2003 | Arnold | |
| 2003/0226091 A1 | 12/2003 | Platenberg et al. | |
| 2004/0019313 A1 | 1/2004 | Childers et al. | |
| 2004/0037724 A1 | 2/2004 | Haser et al. | |
| 2004/0069926 A1 * | 4/2004 | Ward | E04G 17/04 249/210 |
| 2004/0097868 A1 | 5/2004 | Kadziauskas et al. | |
| 2004/0106915 A1 * | 6/2004 | Thoe | A61B 17/00 606/1 |
| 2004/0124157 A1 | 7/2004 | Briggs et al. | |
| 2004/0127840 A1 | 7/2004 | Gara et al. | |
| 2004/0190971 A1 * | 9/2004 | Tanaka | B41J 15/044 400/615.2 |
| 2004/0193182 A1 | 9/2004 | Yaguchi et al. | |

(56) References Cited

U.S. PATENT DOCUMENTS

| | | | |
|---|---|---|---|
| 2004/0202561 A1* | 10/2004 | Hershberger | A61M 1/0064 417/477.7 |
| 2004/0212344 A1 | 10/2004 | Tamura et al. | |
| 2004/0215127 A1 | 10/2004 | Kadziauskas et al. | |
| 2004/0224641 A1 | 11/2004 | Sinn | |
| 2004/0253129 A1 | 12/2004 | Sorensen et al. | |
| 2005/0039567 A1 | 2/2005 | Peterson et al. | |
| 2005/0054971 A1 | 3/2005 | Steen et al. | |
| 2005/0069419 A1* | 3/2005 | Cull | F04B 43/1276 417/53 |
| 2005/0070859 A1 | 3/2005 | Cull et al. | |
| 2005/0070871 A1 | 3/2005 | Lawton et al. | |
| 2005/0095153 A1 | 5/2005 | Demers et al. | |
| 2005/0103607 A1 | 5/2005 | Mezhinsky | |
| 2005/0109595 A1 | 5/2005 | Mezhinsky et al. | |
| 2005/0118048 A1 | 6/2005 | Traxinger | |
| 2005/0119679 A1 | 6/2005 | Rabiner et al. | |
| 2005/0130098 A1 | 6/2005 | Warner | |
| 2005/0187513 A1 | 8/2005 | Rabiner et al. | |
| 2005/0197131 A1 | 9/2005 | Ikegami | |
| 2005/0209552 A1 | 9/2005 | Beck et al. | |
| 2005/0228266 A1 | 10/2005 | McCombs | |
| 2005/0236936 A1 | 10/2005 | Shiv et al. | |
| 2005/0245888 A1 | 11/2005 | Cull | |
| 2005/0261628 A1 | 11/2005 | Boukhny et al. | |
| 2005/0267504 A1 | 12/2005 | Boukhny et al. | |
| 2006/0035585 A1 | 2/2006 | Washiro | |
| 2006/0036180 A1 | 2/2006 | Boukhny et al. | |
| 2006/0041220 A1 | 2/2006 | Boukhny et al. | |
| 2006/0046659 A1 | 3/2006 | Haartsen et al. | |
| 2006/0074405 A1 | 4/2006 | Malackowski et al. | |
| 2006/0078448 A1 | 4/2006 | Holden | |
| 2006/0114175 A1 | 6/2006 | Boukhny | |
| 2006/0145540 A1 | 7/2006 | Mezhinsky | |
| 2006/0219049 A1 | 10/2006 | Horvath et al. | |
| 2006/0219962 A1 | 10/2006 | Dancs et al. | |
| 2006/0236242 A1 | 10/2006 | Boukhny et al. | |
| 2007/0016174 A1 | 1/2007 | Millman et al. | |
| 2007/0049898 A1 | 3/2007 | Hopkins et al. | |
| 2007/0060926 A1 | 3/2007 | Escaf | |
| 2007/0073214 A1 | 3/2007 | Dacquay et al. | |
| 2007/0073309 A1 | 3/2007 | Kadziauskas et al. | |
| 2007/0078379 A1 | 4/2007 | Boukhny et al. | |
| 2007/0085611 A1 | 4/2007 | Gerry et al. | |
| 2007/0107490 A1 | 5/2007 | Artsyukhovich et al. | |
| 2007/0231205 A1 | 10/2007 | Williams et al. | |
| 2007/0233003 A1 | 10/2007 | Radgowski et al. | |
| 2007/0248477 A1 | 10/2007 | Nazarifar et al. | |
| 2007/0249942 A1 | 10/2007 | Salehi et al. | |
| 2007/0252395 A1 | 11/2007 | Williams et al. | |
| 2007/0253463 A1* | 11/2007 | Perry | A61M 1/369 374/208 |
| 2008/0015493 A1* | 1/2008 | Childers | A61M 1/3644 604/29 |
| 2008/0027368 A1* | 1/2008 | Kollar | A61M 1/3666 604/6.14 |
| 2008/0033342 A1 | 2/2008 | Staggs | |
| 2008/0066542 A1 | 3/2008 | Gao | |
| 2008/0082040 A1 | 4/2008 | Kubler et al. | |
| 2008/0112828 A1 | 5/2008 | Muri et al. | |
| 2008/0114289 A1* | 5/2008 | Muri | A61F 9/00745 604/30 |
| 2008/0114290 A1 | 5/2008 | King et al. | |
| 2008/0114291 A1 | 5/2008 | Muri et al. | |
| 2008/0114300 A1 | 5/2008 | Muri et al. | |
| 2008/0114311 A1* | 5/2008 | Muri | A61M 1/72 604/294 |
| 2008/0114387 A1 | 5/2008 | Hertweck et al. | |
| 2008/0125694 A1 | 5/2008 | Domash | |
| 2008/0125695 A1 | 5/2008 | Hopkins et al. | |
| 2008/0125697 A1 | 5/2008 | Gao | |
| 2008/0125698 A1 | 5/2008 | Gerg et al. | |
| 2008/0129695 A1 | 6/2008 | Li | |
| 2008/0146989 A1 | 6/2008 | Zacharias | |
| 2008/0200878 A1 | 8/2008 | Davis et al. | |
| 2008/0243105 A1 | 10/2008 | Horvath | |
| 2008/0262476 A1 | 10/2008 | Krause et al. | |
| 2008/0281253 A1 | 11/2008 | Injev et al. | |
| 2008/0294087 A1 | 11/2008 | Steen et al. | |
| 2008/0312594 A1 | 12/2008 | Urich et al. | |
| 2009/0005712 A1 | 1/2009 | Raney | |
| 2009/0005789 A1 | 1/2009 | Charles | |
| 2009/0048607 A1 | 2/2009 | Rockley | |
| 2009/0087327 A1 | 4/2009 | Voltenburg, Jr. et al. | |
| 2009/0124974 A1 | 5/2009 | Crank et al. | |
| 2009/0163853 A1 | 6/2009 | Cull et al. | |
| 2010/0036256 A1 | 2/2010 | Boukhny et al. | |
| 2010/0057016 A1 | 3/2010 | Dale et al. | |
| 2010/0069825 A1 | 3/2010 | Raney | |
| 2010/0069828 A1 | 3/2010 | Steen et al. | |
| 2010/0140149 A1 | 6/2010 | Fulkerson et al. | |
| 2010/0152685 A1 | 6/2010 | Goh | |
| 2010/0185150 A1 | 7/2010 | Zacharias | |
| 2010/0249693 A1 | 9/2010 | Links | |
| 2010/0280435 A1 | 11/2010 | Raney et al. | |
| 2011/0092887 A1 | 4/2011 | Wong et al. | |
| 2011/0092924 A1 | 4/2011 | Wong et al. | |
| 2011/0092962 A1 | 4/2011 | Ma et al. | |
| 2011/0098721 A1 | 4/2011 | Tran et al. | |
| 2011/0160646 A1 | 6/2011 | Kadziauskas et al. | |
| 2011/0208047 A1 | 8/2011 | Fago | |
| 2011/0251569 A1 | 10/2011 | Turner et al. | |
| 2011/0295193 A1* | 12/2011 | Fitzgerald | A61F 9/00736 604/22 |
| 2011/0300010 A1 | 12/2011 | Jarnagin et al. | |
| 2012/0065580 A1 | 3/2012 | Gerg et al. | |
| 2012/0078181 A1 | 3/2012 | Smith et al. | |
| 2012/0083735 A1 | 4/2012 | Pfouts | |
| 2012/0083736 A1* | 4/2012 | Pfouts | A61M 5/14232 604/151 |
| 2012/0083800 A1 | 4/2012 | Andersohn et al. | |
| 2013/0071272 A1* | 3/2013 | Juretich | F04B 43/1276 417/477.2 |
| 2013/0072853 A1 | 3/2013 | Wong et al. | |
| 2013/0169412 A1 | 7/2013 | Roth | |
| 2013/0184638 A1 | 7/2013 | Scarpaci et al. | |
| 2013/0184676 A1 | 7/2013 | Kamen et al. | |
| 2013/0245543 A1 | 9/2013 | Gerg et al. | |
| 2013/0267892 A1 | 10/2013 | Woolford et al. | |
| 2013/0289475 A1 | 10/2013 | Muri et al. | |
| 2013/0303978 A1 | 11/2013 | Ross | |
| 2013/0336814 A1 | 12/2013 | Kamen et al. | |
| 2014/0088558 A1 | 3/2014 | Holtwick et al. | |
| 2014/0178215 A1 | 6/2014 | Baxter et al. | |
| 2014/0188076 A1 | 7/2014 | Kamen et al. | |
| 2014/0276424 A1 | 9/2014 | Davis et al. | |
| 2016/0151564 A1 | 6/2016 | Magers et al. | |

FOREIGN PATENT DOCUMENTS

| | | |
|---|---|---|
| EP | 56019 A1 | 7/1982 |
| EP | 0124687 A2 | 11/1984 |
| EP | 0270819 A2 | 6/1988 |
| EP | 424687 A1 | 5/1991 |
| EP | 0519993 A1 | 12/1992 |
| EP | 0619993 A1 | 10/1994 |
| EP | 1010437 A1 | 6/2000 |
| EP | 1072285 A1 | 1/2001 |
| EP | 1113562 A1 | 7/2001 |
| EP | 1464310 A1 | 10/2004 |
| EP | 1469440 A2 | 10/2004 |
| EP | 1550406 A2 | 7/2005 |
| EP | 1704839 A1 | 9/2006 |
| EP | 1779879 A1 | 5/2007 |
| EP | 1787606 A1 | 5/2007 |
| EP | 1849443 A1 | 10/2007 |
| EP | 1849444 A1 | 10/2007 |
| EP | 1857128 A1 | 11/2007 |
| EP | 1310267 B1 | 1/2008 |
| EP | 1873501 A1 | 1/2008 |
| EP | 1900347 A1 | 3/2008 |
| EP | 1925274 A2 | 5/2008 |
| EP | 1867349 B1 | 11/2008 |

(56) References Cited

FOREIGN PATENT DOCUMENTS

| | | | |
|---|---|---|---|
| EP | 2298221 A1 | 3/2011 | |
| ES | 2264369 A1 | 12/2006 | |
| GB | 2230301 A | 10/1990 | |
| GB | 2352887 A | 2/2001 | |
| GB | 2438679 A | 12/2007 | |
| JP | S5724482 A | 2/1982 | |
| JP | S58167333 A | 10/1983 | |
| JP | S62204463 A | 9/1987 | |
| JP | H0585585 A * | 4/1993 | ........... B65D 85/575 |
| JP | 2005195653 A | 7/2005 | |
| JP | 2008188110 A | 8/2008 | |
| WO | 9220310 A1 | 11/1992 | |
| WO | 9315777 A2 | 8/1993 | |
| WO | 9317729 A1 | 9/1993 | |
| WO | 9324082 A1 | 12/1993 | |
| WO | 9405346 A1 | 3/1994 | |
| WO | 9613216 A1 | 5/1996 | |
| WO | 9632144 A1 | 10/1996 | |
| WO | 9737700 A1 | 10/1997 | |
| WO | 9818507 A1 | 5/1998 | |
| WO | 9917818 A1 | 4/1999 | |
| WO | 0000096 A1 | 1/2000 | |
| WO | 0070225 A1 | 11/2000 | |
| WO | 2007143797 A1 | 12/2000 | |
| WO | 0122696 A1 | 3/2001 | |
| WO | 0226286 A2 | 4/2002 | |
| WO | 0228449 A2 | 4/2002 | |
| WO | 0234314 A1 | 5/2002 | |
| WO | 03102878 A1 | 12/2003 | |
| WO | 04096360 A1 | 11/2004 | |
| WO | 2004114180 A1 | 12/2004 | |
| WO | 05084728 A2 | 9/2005 | |
| WO | 0509203 A2 | 10/2005 | |
| WO | 05092047 A2 | 10/2005 | |
| WO | 06101908 A2 | 9/2006 | |
| WO | 06125280 A1 | 11/2006 | |
| WO | 2007121144 A1 | 10/2007 | |
| WO | 2007143677 A2 | 12/2007 | |
| WO | 2007149637 A2 | 12/2007 | |
| WO | 2008030872 A1 | 3/2008 | |
| WO | 2008060859 A1 | 5/2008 | |
| WO | 2008060902 A1 | 5/2008 | |
| WO | 2008060995 A1 | 5/2008 | |
| WO | 2009123547 A1 | 10/2009 | |
| WO | 2010054146 A1 | 5/2010 | |
| WO | 2010054225 A2 | 5/2010 | |
| WO | 2010151704 A1 | 12/2010 | |
| WO | 2012151062 A1 | 11/2012 | |
| WO | 2013142009 A1 | 9/2013 | |
| WO | 2015009945 A1 | 1/2015 | |

OTHER PUBLICATIONS

European Search Report for Application No. EP16202917, dated May 2, 2017, 6 pages.
International Search Report and Written Opinion for Application No. PCT/US2015/058655, dated Jan. 28, 2016, 13 pages.
International Search Report and Written Opinion for Application No. PCT/US2015/066036, dated Jul. 4, 2016, 20 pages.
International Search Report and Written Opinion for Application No. PCT/US2016/049970, dated Dec. 5, 2016, 12 pages.
International Search Report and Written Opinion for Application No. PCT/US2016/061648, dated Feb. 7, 2017, 12 pages.

* cited by examiner

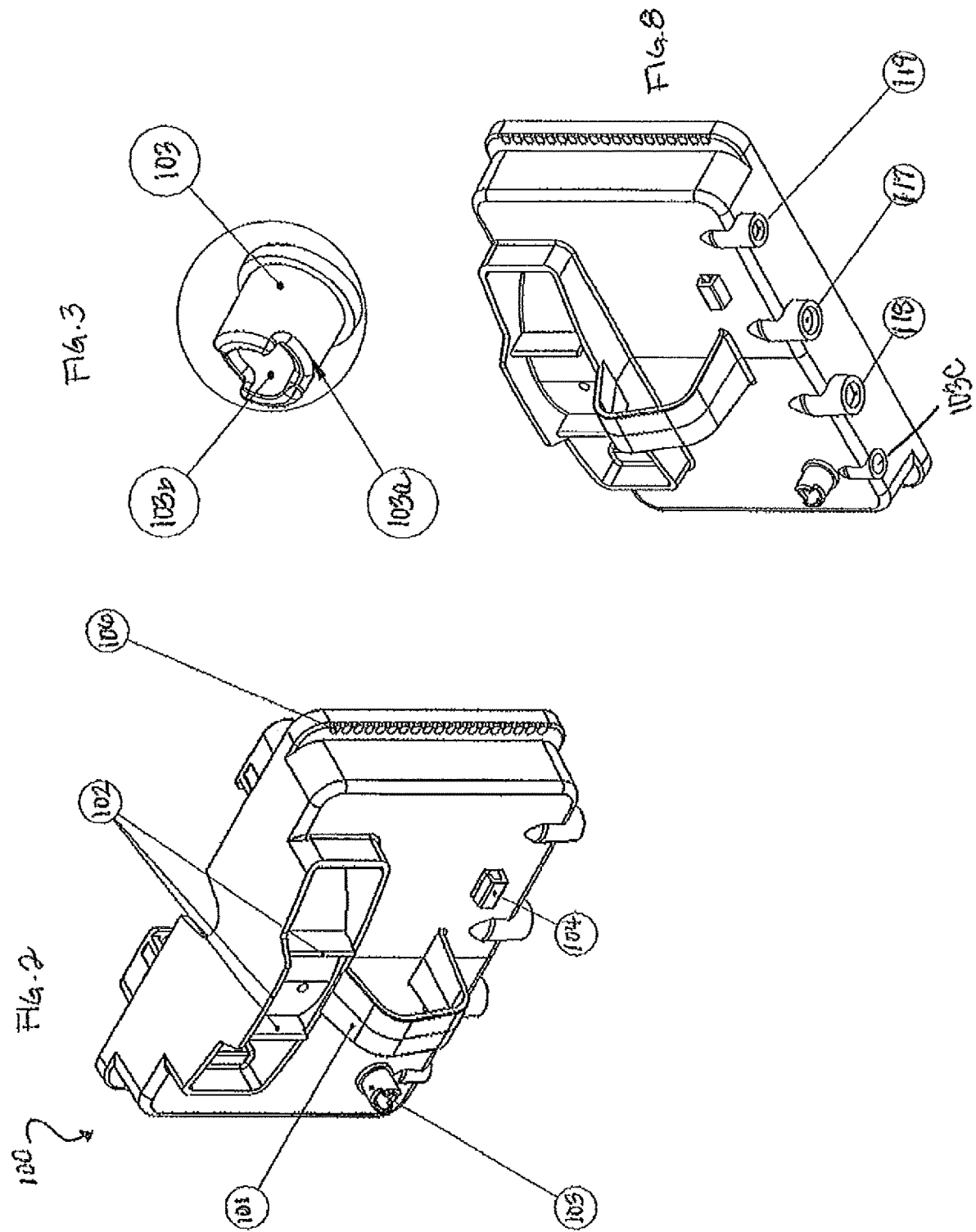

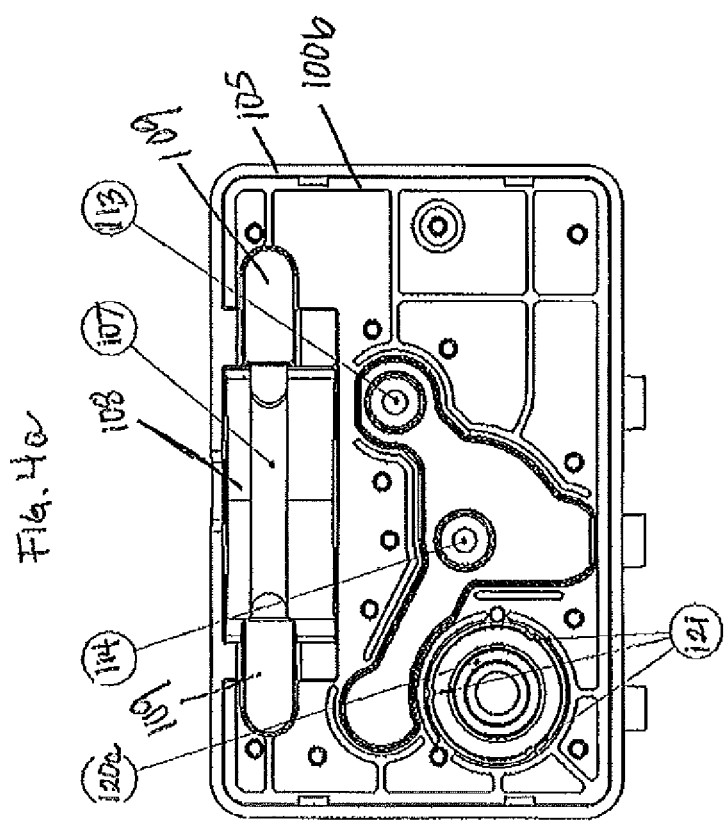

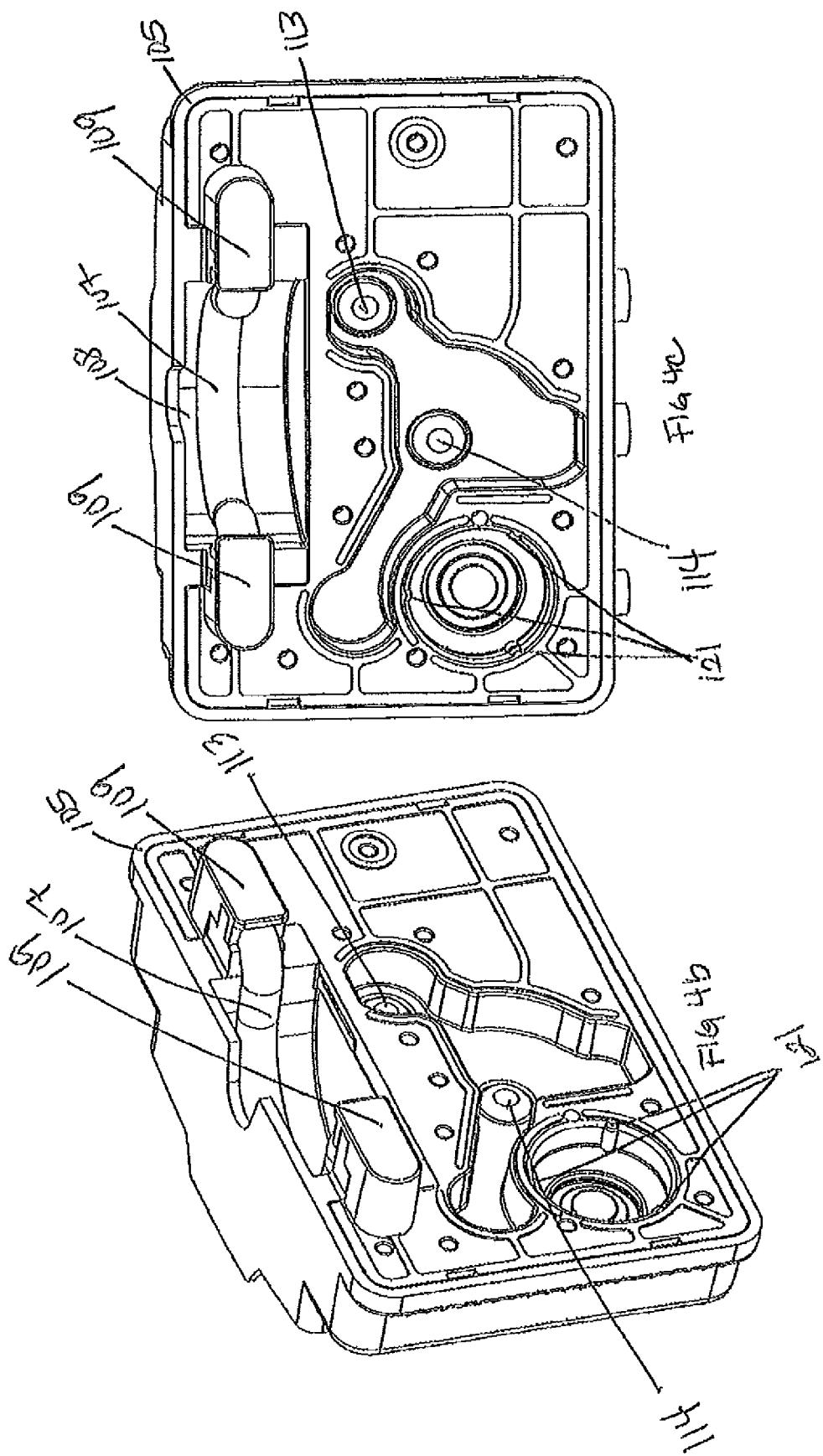

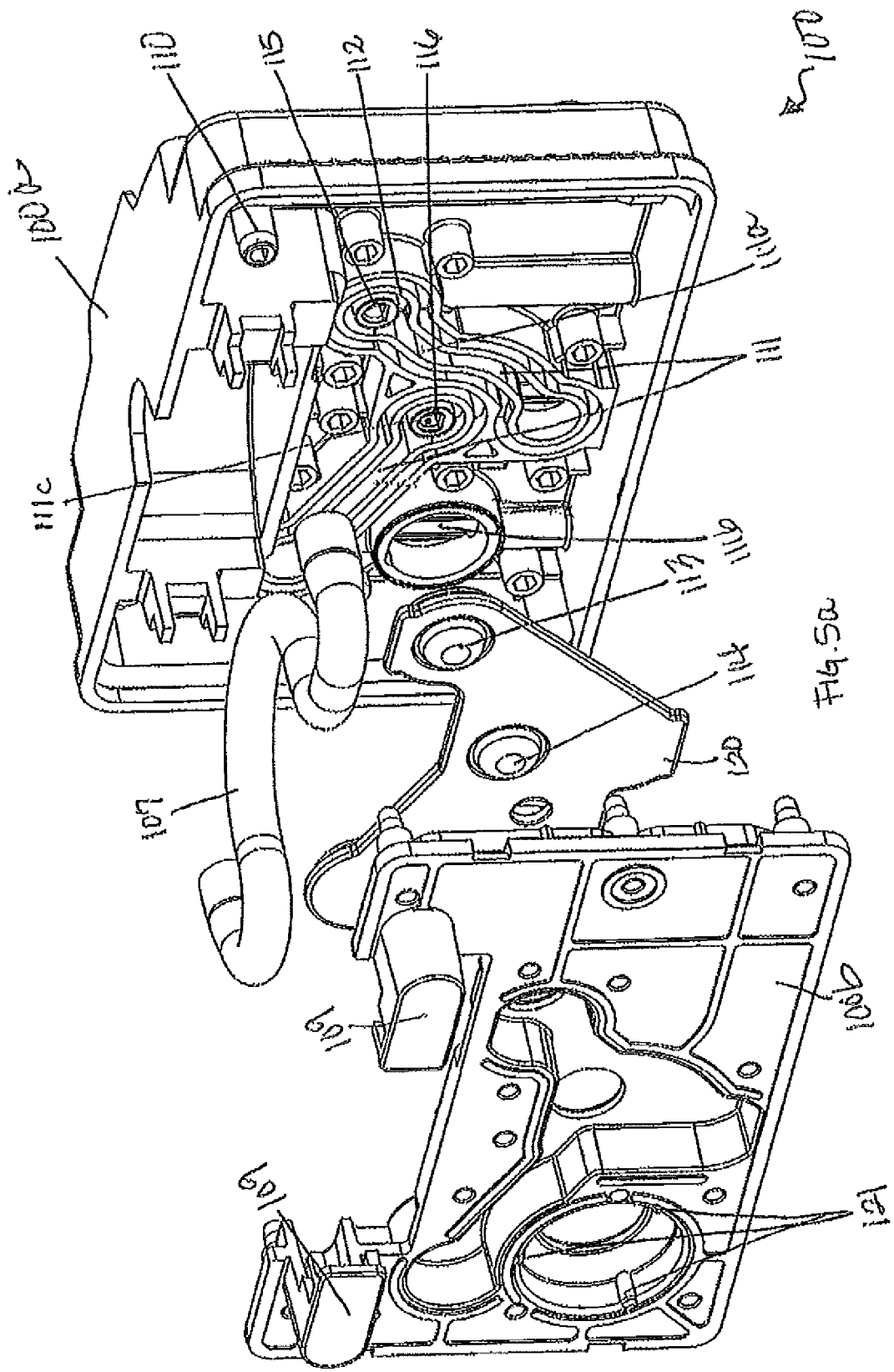

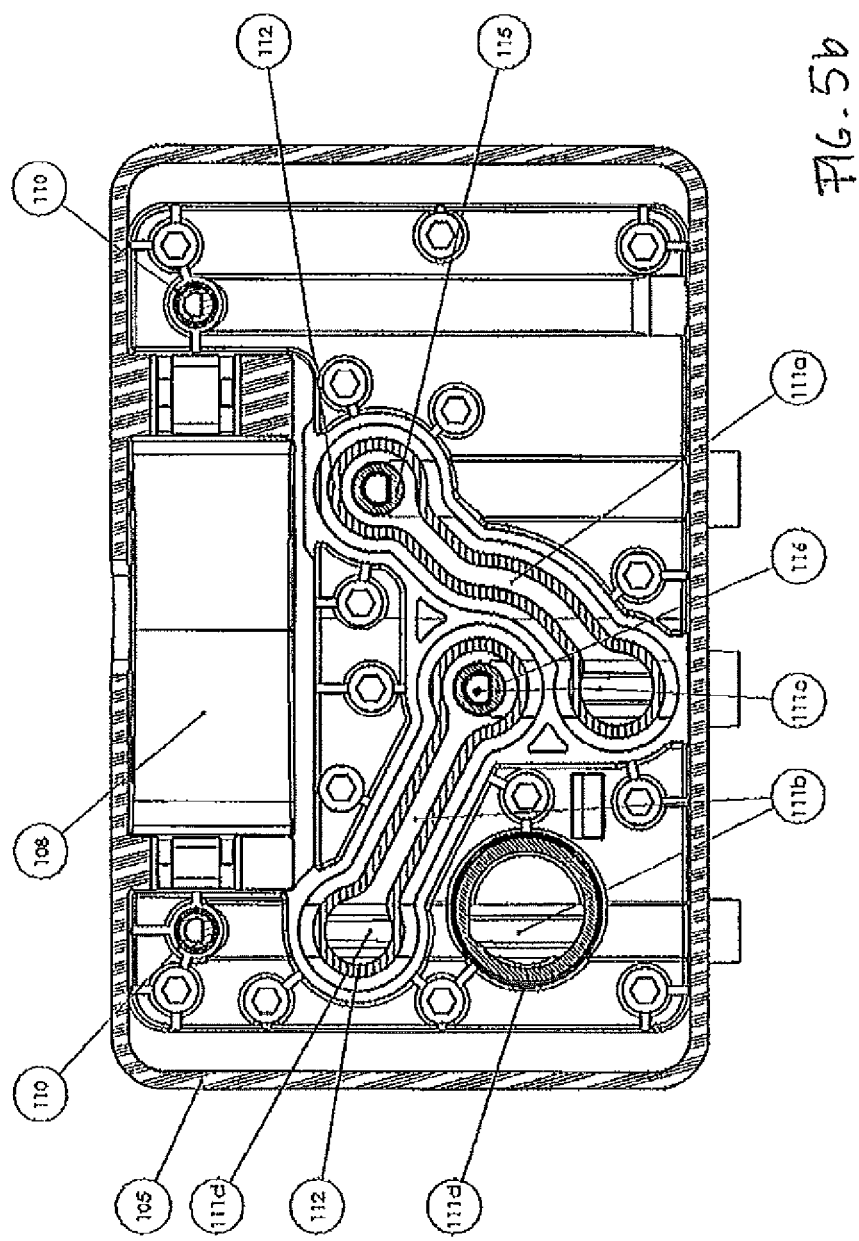

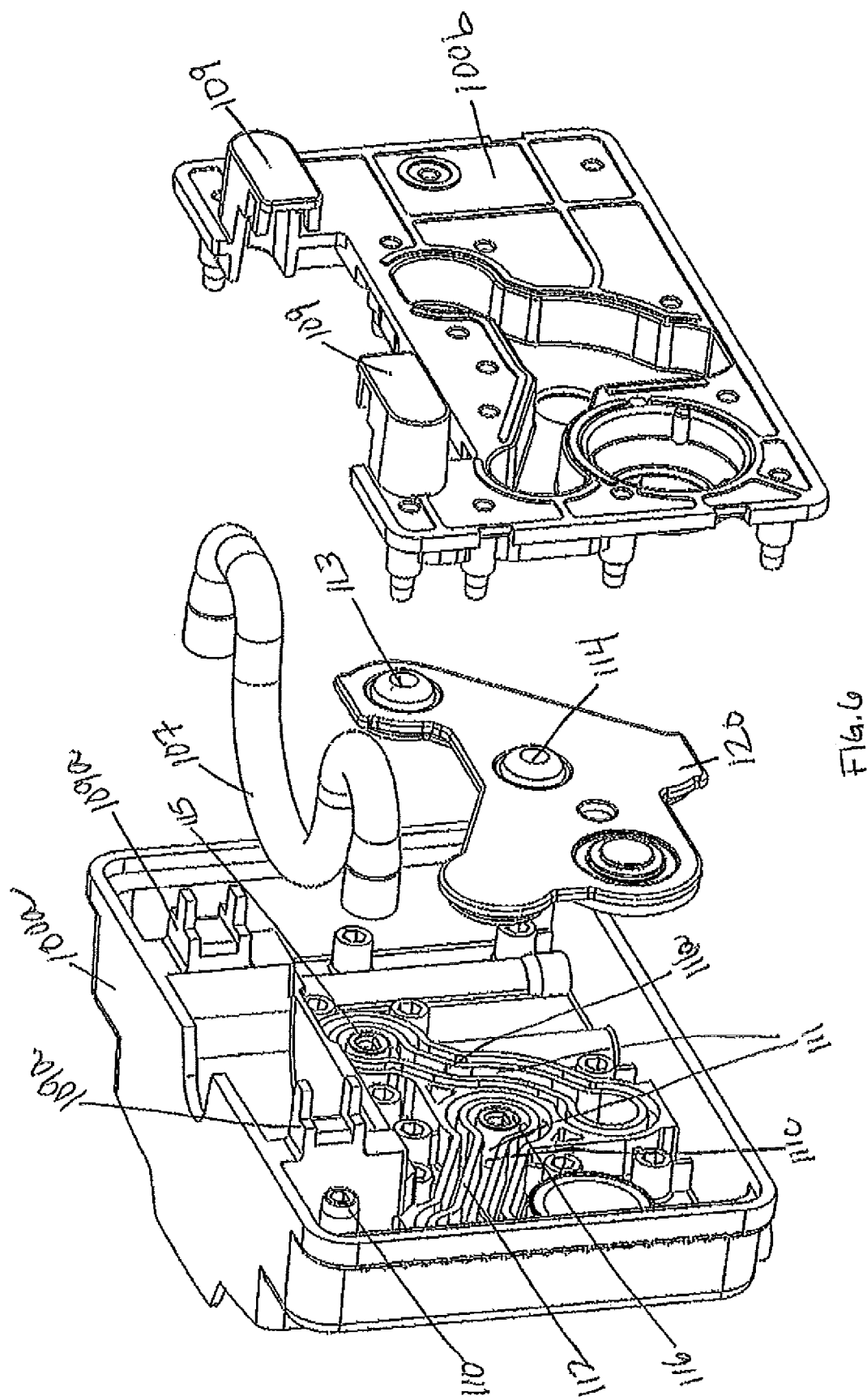

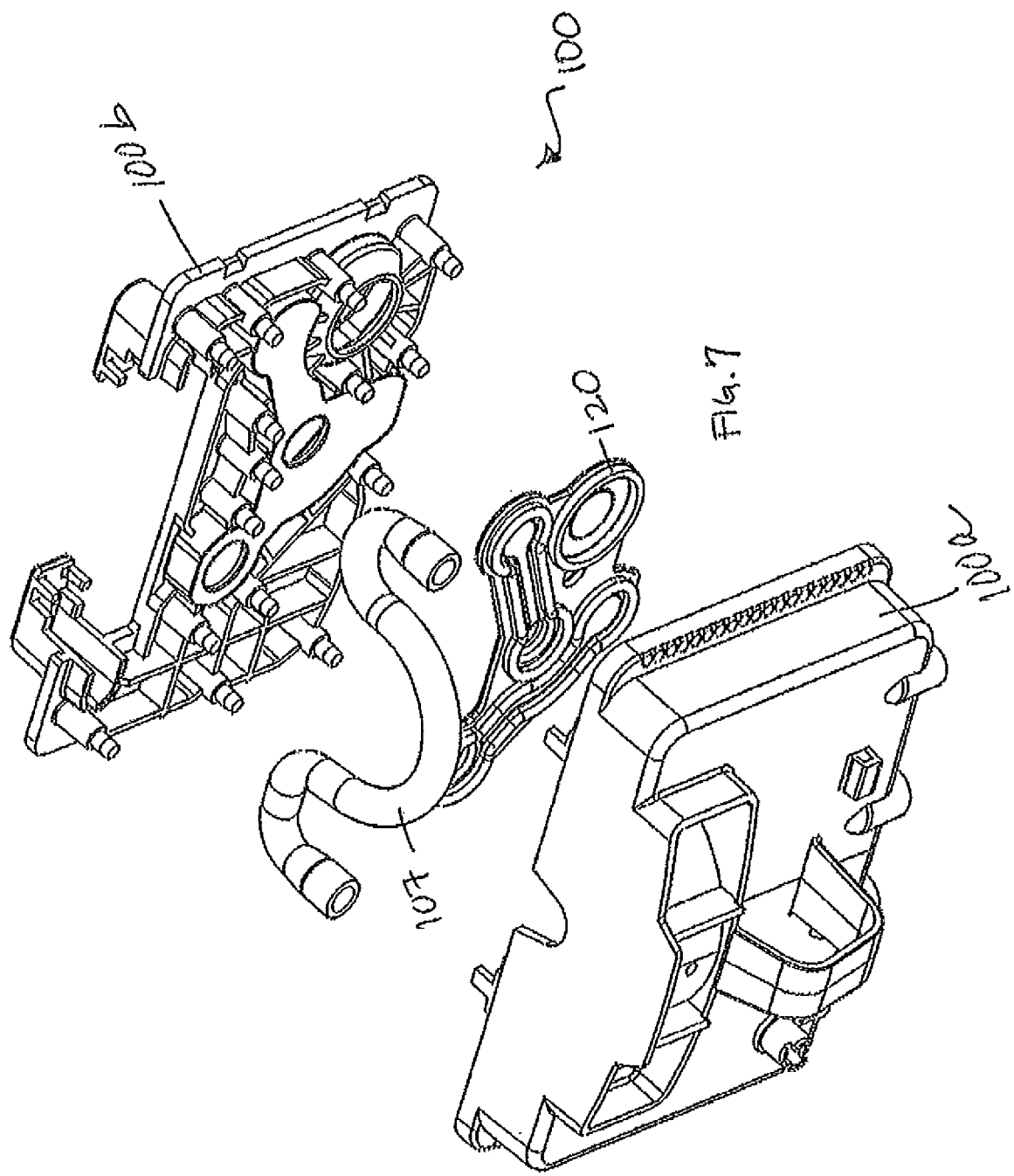

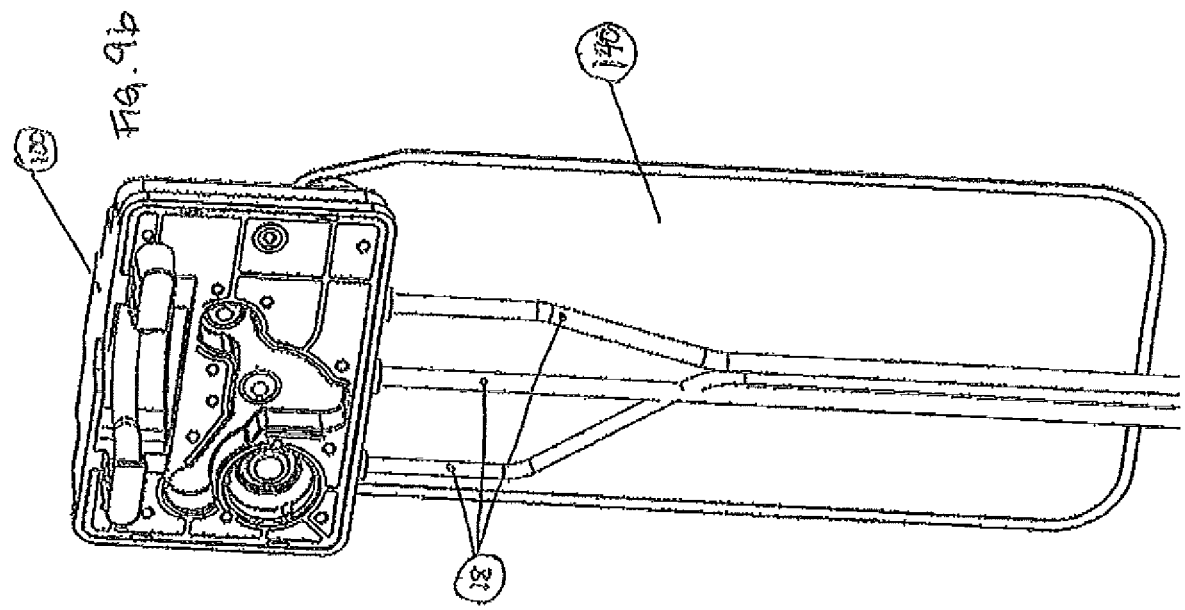
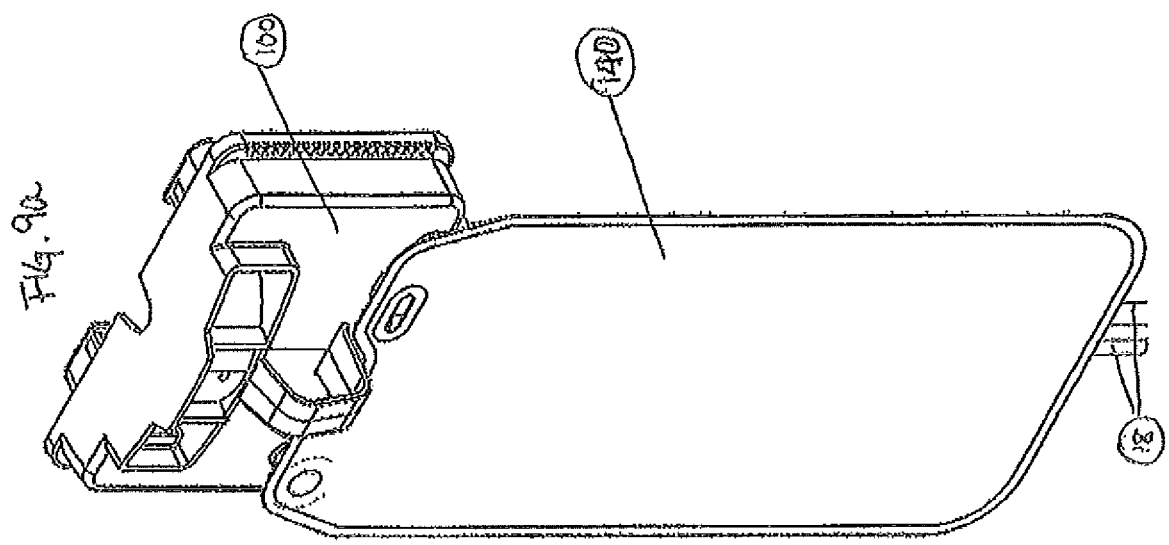

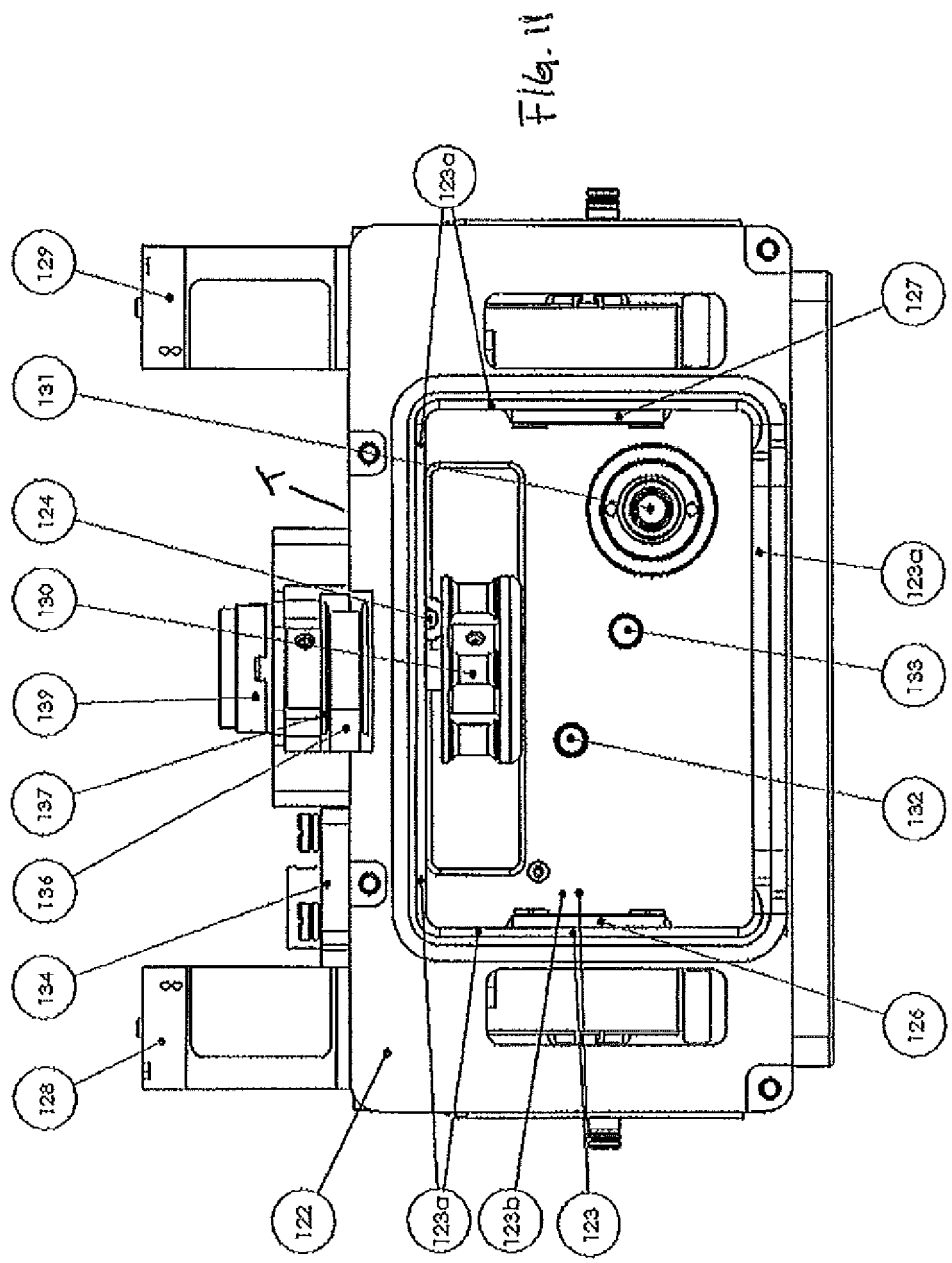

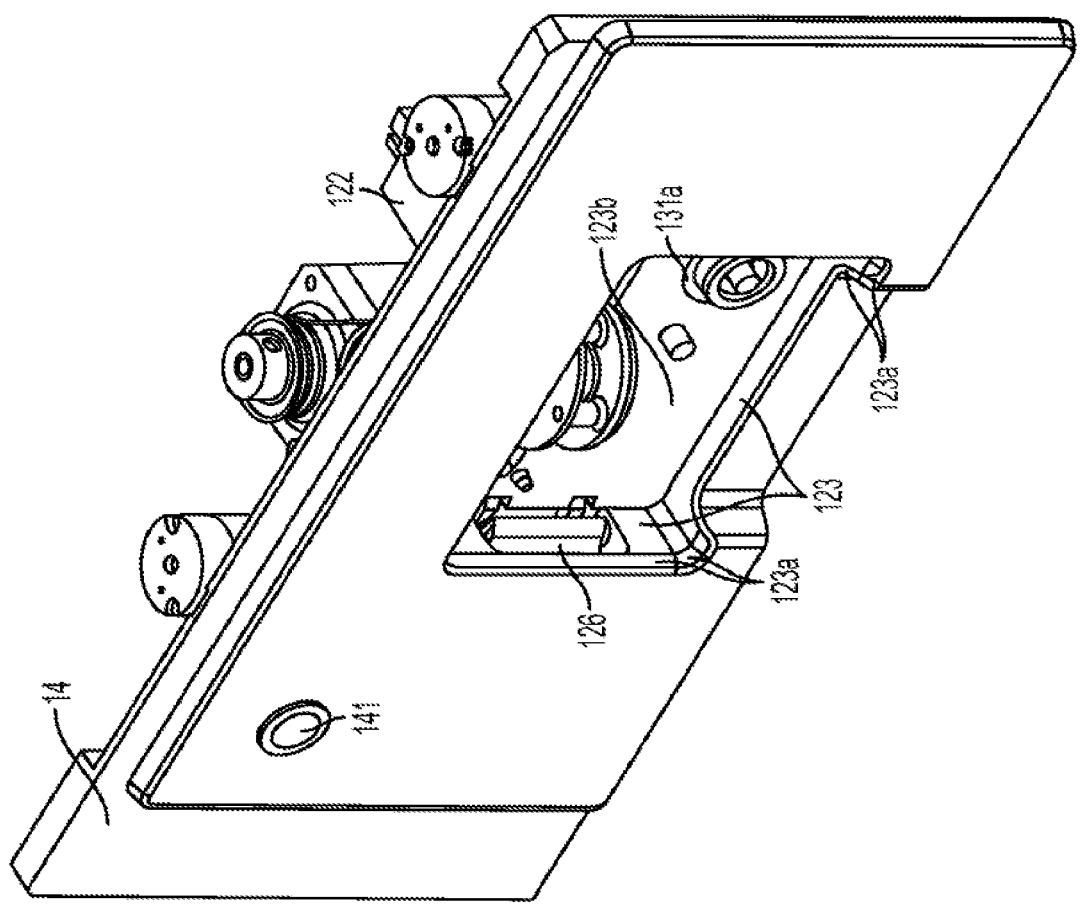

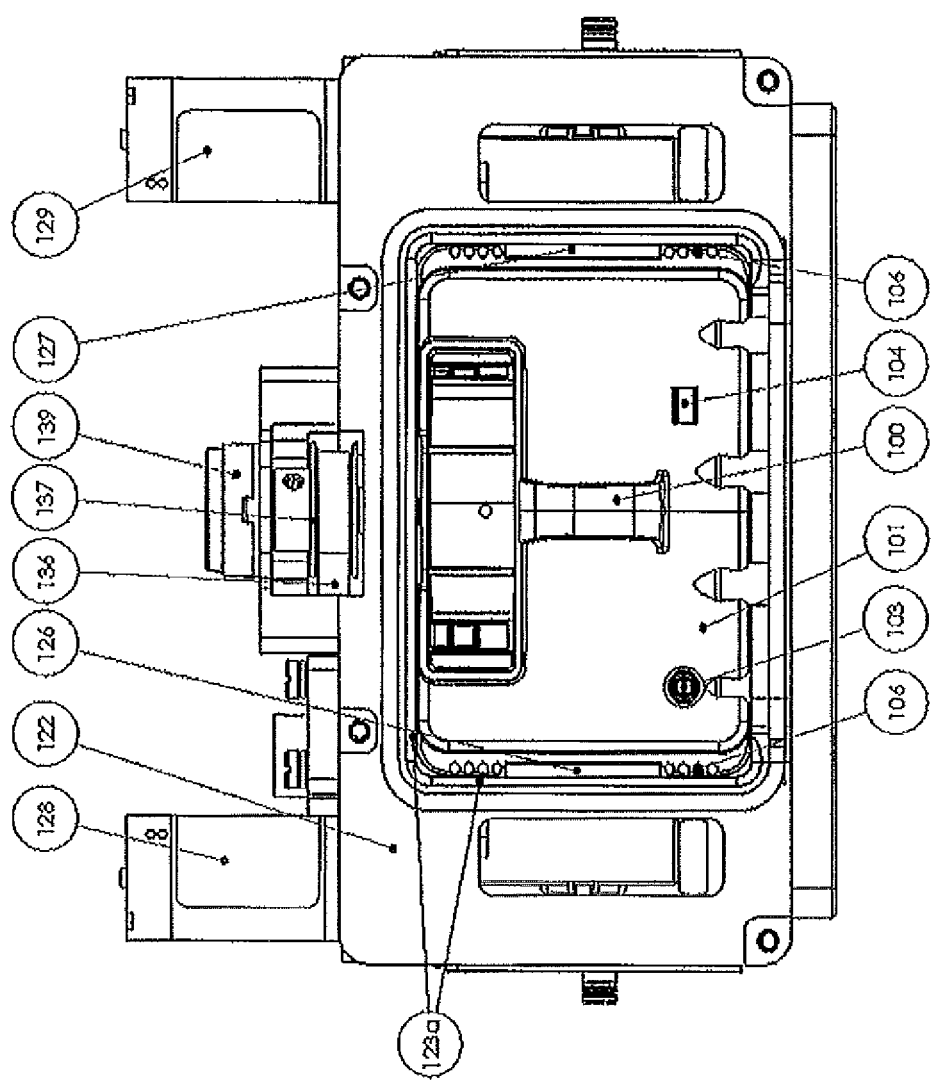

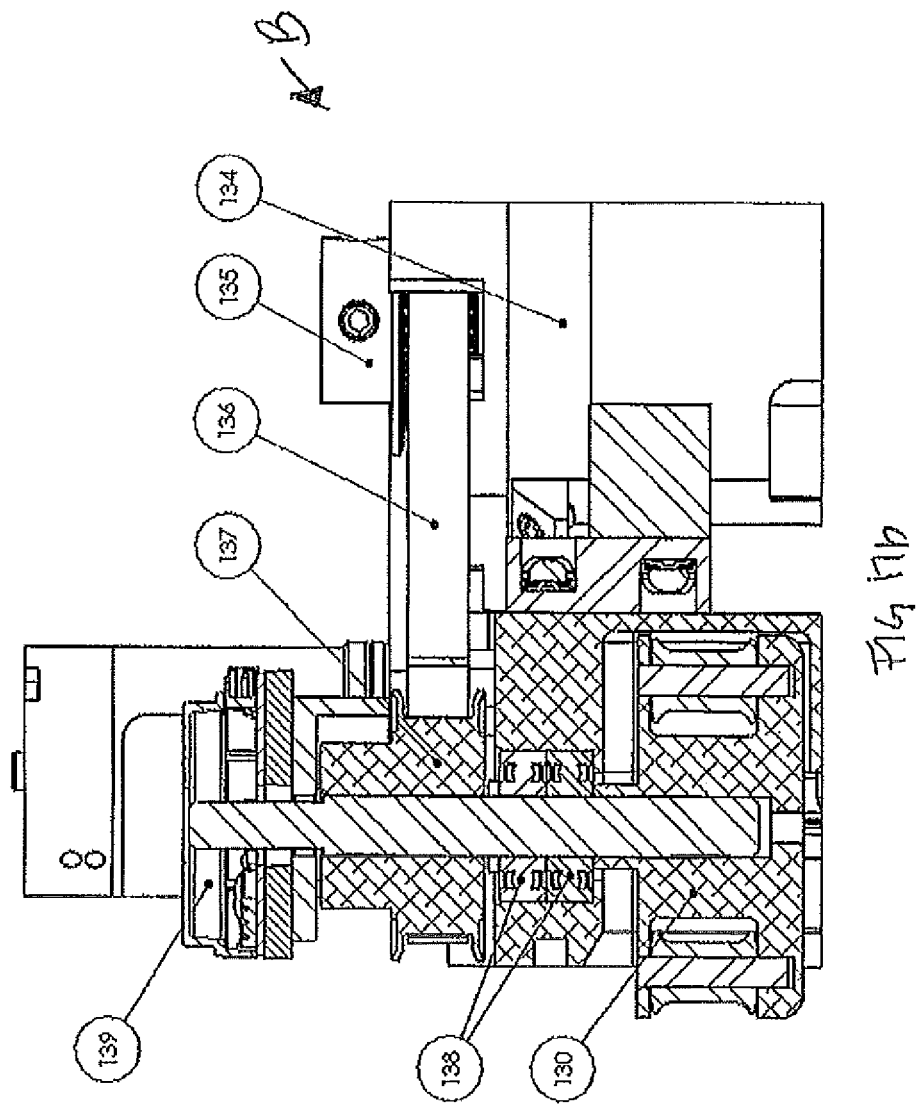

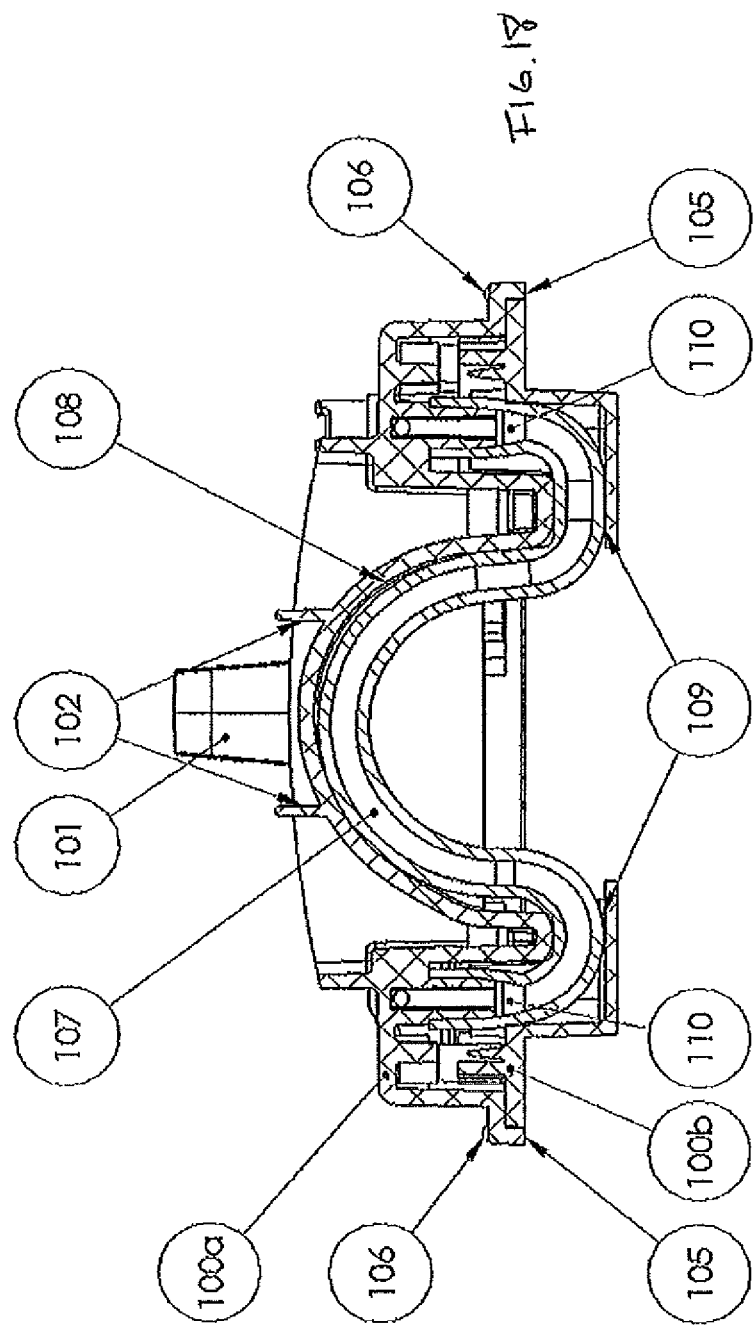

PRE-ALIGNMENT SURGICAL CASSETTE INTERFACE

CROSS-REFERENCE TO RELATED APPLICATIONS

This application claims priority to and is a divisional of U.S. patent application Ser. No. 13/944,726, filed Jul. 17, 2013, which is a continuation-in-part of U.S. patent application Ser. No. 13/776,988, filed on Feb. 26, 2013, which claims priority to U.S. provisional application No. 61/612,307, entitled "Surgical Cassette", filed on Mar. 17, 2012, the entire contents of which are hereby incorporated by reference in their entirety for all purposes as if fully set forth herein.

TECHNICAL FIELD OF THE INVENTION

The present invention is generally related to methods, devices, and systems for pre-aligning a surgical cassette for providing surgical fluid flows, particularly during treatment of an eye.

BACKGROUND OF THE INVENTION

The optical elements of the eye include both a cornea (at the front of the eye) and a lens within the eye. The lens and cornea work together to focus light onto the retina at the back of the eye. The lens also changes in shape, adjusting the focus of the eye to vary between viewing near objects and far objects. The lens is found just behind the pupil, and within a capsular bag. This capsular bag is a thin, relatively delicate structure which separates the eye into anterior and posterior chambers.

With age, clouding of the lens or cataracts are fairly common. Cataracts may form in the hard central nucleus of the lens, in the softer peripheral cortical portion of the lens, or at the back of the lens near the capsular bag.

Cataracts can be treated by the replacement of the cloudy lens with an artificial lens. Phacoemulsification systems often use ultrasound energy to fragment the lens and aspirate the lens material from within the capsular bag. This may allow the capsular bag to be used for positioning of the artificial lens, and maintains the separation between the anterior portion of the eye and the vitreous humour in the posterior chamber of the eye.

During cataract surgery and other therapies of the eye, accurate control over the volume of fluid within the eye is highly beneficial. For example, while ultrasound energy breaks up the lens and allows it to be drawn into a treatment probe with an aspiration flow, a corresponding irrigation flow may be introduced into the eye so that the total volume of fluid in the eye does not change excessively. If the total volume of fluid in the eye is allowed to get too low at any time during the procedure, the eye may collapse and cause significant tissue damage. Similarly, excessive pressure within the eye may strain and injure tissues of the eye.

While a variety of specific fluid transport mechanisms have been used in phacoemulsification and other treatment systems for the eyes, aspiration flow systems can generally be classified in two categories: 1) volumetric-based aspiration flow systems using positive displacement pumps; and 2) vacuum-based aspiration systems using a vacuum source, typically applied to the aspiration flow through an air-liquid interface. These two categories of aspiration flow systems each have unique characteristics that render one more suitable for some procedures than the other, and vice versa.

Among positive displacement aspiration systems, peristaltic pumps (which use rotating rollers that press against a flexible tubing to induce flow) are commonly employed. Such pumps provide accurate control over the flow volume. The pressure of the flow, however, is less accurately controlled and the variations in vacuum may result in the feel or traction of the handpiece varying during a procedure. Peristaltic and other displacement pump systems may also be somewhat slow.

Vacuum-based aspiration systems provide accurate control over the fluid pressure within the eye, particularly when combined with gravity-fed irrigation systems. While vacuum-based systems can result in excessive fluid flows in some circumstances, they provide advantages, for example, when removing a relatively large quantity of the viscous vitreous humour from the posterior chamber of the eye. However, Venturi pumps and other vacuum-based aspiration flow systems are subject to pressure surges during occlusion of the treatment probe, and such pressure surges may decrease the surgeon's control over the eye treatment procedure.

Different tissues may be aspirated from the anterior chamber of the eye with the two different types of aspiration flow. For example, vacuum-induced aspiration flow may quickly aspirate tissues at a significant distance from a delicate structure of the eye (such as the capsular bag), while tissues that are closer to the capsular bag are aspirated more methodically using displacement-induced flows.

Conventionally, fluid aspiration systems include a console and a fluidic cassette mounted on the console. The fluidic cassette is typically changed for each patient and cooperates with the console to provide fluid aspiration. Generally, a single type of cassette is used by a particular console, regardless of whether the procedure will require positive displacement aspiration, vacuum-based aspiration, or both. U.S. Pat. No. 8,070,712; U.S. Published Application 2008011431; and U.S. Published Application 20080114291 provide examples of cassettes currently used in the marketplace, the contents of each are herewith incorporated by reference in their entirety as if set forth herein.

Such a cassette is typically physically mated to the afore-discussed console. In providing the physical association between the cassette and the console, at least the aspiration/pumping aspects discussed above must be properly aligned as between the cassette and the console, at least in order to provide proper functionality to the fluidics systems. As such, misalignment may lead to system malfunction, inoperability, or poor performance. However, currently available systems that provide for the alignment of placement and attitude of the cassette onto the console suffer from a variety of issues, including jamming, breakage, and inability to assess a sound alignment and cassette attitude, among others.

More particularly, the surgical cassette may be inadvertently or deliberately mis-loaded into the receiving interface of the console. This mis-loading may occur in such a way so as to cause jamming of the cassette between the side-clamps that are interior to the receiving area of the console and are provided to receive the cassette. A mis-load may particularly occur when the planar attitude of the cassette is tilted rotationally toward the left or right of the receiving area of the console. Although misalignment occurs less frequently as expertise in use of the console increases, even the most expert users experience an occasional mis-load.

In the known art, alignment features may thus be provided, such as an "alignment key" on one of the console receiving area or the cassette, or exterior clamps, such as on the exterior portion of the console and on the top and bottom of the receiving area. However, these solutions in the known art still frequently suffer from jamming due to misalignment, such as due to inadvertent misalignment of the alignment key or improper orientation with respect to one of the top clamp or the bottom clamp. Additionally, these solutions fail to provide suitable for handling of the administration tubing that typical provides the fluid aspiration discussed above.

In light of the above, it would be advantageous to provide improved devices, systems, and methods for eye surgery.

SUMMARY OF THE INVENTION

The present invention provides a phacoemulsification surgical console, and a related system and method. The console may include a cassette receiver suitable for receiving a surgical cassette, a controller suitable for controlling provided aspects of the phacoemulsification; and a pre-alignment feature along a lower portion under and proximate to the cassette receiver, extending outwardly from the lower portion, and suitable for aligning the surgical cassette to the cassette receiver. The pre-alignment feature may comprise a shelf.

A method in accordance with the invention may include receiving a bottom portion of a cassette upon a pre-alignment feature adjacent to a lower portion of a cassette receiver of the console, and receiving a top portion of the cassette into an upper portion of the cassette receiver upon rotation of the top portion of the cassette into the upper portion of the cassette receiver about an axis along contact points between the cassette and the pre-alignment feature. The method may further include clamping the cassette into the cassette receiver following an aligned receiving of the bottom portion and an aligned receiving of the top portion. The method may further include ejecting the cassette following use following the receiving steps, and the cassette may rest at least partially on the pre-alignment feature following the ejecting.

A phacoemulsification system according to the invention may include a surgical cassette and a surgical console. The surgical console may include a cassette receiver suitable for receiving the surgical cassette, a controller suitable for controlling provided aspects of the phacoemulsification, and a pre-alignment feature along a lower portion under and proximate to the cassette receiver.

Accordingly, the present invention may provide improved devices, systems, and methods for eye surgery.

BRIEF DESCRIPTION OF THE DRAWINGS

The present invention is best understood with reference to the following detailed description of the invention and the drawings in which:

FIG. 2 illustrates an exemplary surgical cassette having a surgical fluid pathway network for use in the system of FIG. 1;

FIG. 3 is a perspective view of an exemplary drain bag port;

FIG. 4*a* is a back view of an exemplary surgical cassette;

FIG. 4*b* is a perspective back view of an exemplary surgical cassette;

FIG. 4*c* is a perspective back view of an exemplary surgical cassette;

FIG. 5*a* is an exploded view of an exemplary surgical cassette;

FIG. 5*b* is a top view of the back of the front plate of an exemplary surgical cassette;

FIG. 6 is an exploded view of an exemplary surgical cassette;

FIG. 7 is an exploded view of an exemplary surgical cassette;

FIG. 8 is a perspective view of the front of an exemplary surgical cassette;

FIG. 9*a* is a perspective view of the front of an exemplary surgical cassette with a drain bag;

FIG. 9*b* is a perspective view of the back of an exemplary surgical cassette with a drain bag and flexible conduit;

FIG. 11 is a top view of an exemplary surgical console;

FIG. 11*a* is a perspective view of the front of an exemplary surgical console;

FIG. 12 is a top view of an exemplary surgical console with a surgical cassette coupled therewith;

FIG. 17*b* is a detailed view of the exemplary peristaltic pump roller assembly (part B) as illustrated in FIG. 17*a*;

FIG. 18 is a cross-sectional view of an exemplary surgical cassette illustrating the peristaltic pump tube and peristaltic pump profile;

DETAILED DESCRIPTION OF THE INVENTION

Reference will now be made in detail to embodiments of the invention, examples of which are illustrated in the accompanying drawings. While the invention will be described in conjunction with the embodiments, it will be understood that they are not intended to limit the invention to those embodiments. On the contrary, the invention is intended to cover alternatives, modifications, and equivalents, which may be included within the spirit and scope of the invention, such as is defined by the appended claims.

Figure 1:
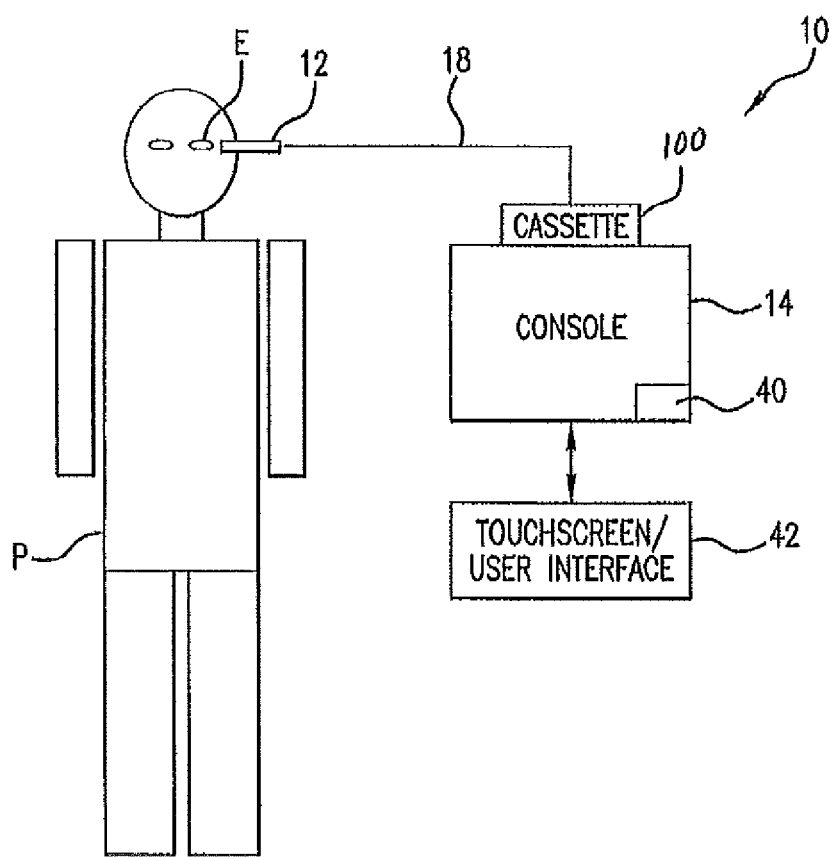
FIG. 1 schematically illustrates an eye treatment system in which a cassette couples an eye treatment probe with an eye treatment console.

Referring to FIG. 1, a system 10 for treating an eye E of a patient P generally includes an eye treatment probe handpiece 12 coupled to a console 14 by a cassette 100 mounted on the console. Handpiece 12 may include a handle for manually manipulating and supporting an insertable probe tip. The probe tip has a distal end which is insertable into the eye, with one or more lumens in the probe tip allowing irrigation fluid to flow from the console 14 and/or cassette 100 into the eye. Aspiration fluid may also be withdrawn through a lumen of the probe tip, with the console 14 and cassette 100 generally including a vacuum aspiration source, a positive displacement aspiration pump, or both to help withdraw and control a flow of surgical fluids into and out of eye E. As the surgical fluids may include biological materials that should not be transferred between patients, cassette 100 will often comprise a disposable (or alternatively, sterilizable) structure, with the surgical fluids being transmitted through flexible conduits 18, also referred to in the pertinent art as administrative tubing, of the cassette that avoid direct contact in between those fluids and the components of console 14.

When a distal end of the probe tip of handpiece 12 is inserted into an eye E, for example, for removal of a lens of a patient with cataracts, an electrical conductor and/or pneumatic line (not shown) may supply energy from console 14 to an ultrasound transmitter of the handpiece, a cutter mechanism, or the like. Alternatively, the handpiece 12 may be configured as an irrigation/aspiration (I/A) or vitrectomy handpiece. Also, the ultrasonic transmitter may be replaced by other means for emulsifying a lens, such as a high energy laser beam. The ultrasound energy from handpiece 12 helps to fragment the tissue of the lens, which can then be drawn into a port of the tip by aspiration flow. So as to balance the volume of material removed by the aspiration flow, an irrigation flow through handpiece 12 (or a separate probe structure) may also be provided, with both the aspiration and irrigations flows being controlled by console 14.

So as to avoid cross-contamination between patients without incurring excessive expenditures for each procedure, cassette 100 and its flexible conduit 18 may be disposable. Alternatively, the flexible conduit or tubing may be disposable, with the cassette body and/or other structures of the cassette being sterilizable. Regardless, the disposable components of the cassette are typically configured for use with a single patient, and may not be suitable for sterilization. The cassette will interface with reusable (and often quite expensive) components of console 14, which may include one or more peristaltic pump rollers, a Venturi or other vacuum source, a controller 40, and the like.

Controller 40 may include an embedded microcontroller and/or many of the components common to a personal computer, such as a processor, data bus, a memory, input and/or output devices (including a touch screen user interface 42), and the like. Controller 40 will often include both hardware and software, with the software typically comprising machine readable code or programming instructions for implementing one, some, or all of the methods described herein. The code may be embodied by a tangible media such as a memory, a magnetic recording media, an optical recording media, or the like. Controller 40 may have (or be coupled to) a recording media reader, or the code may be transmitted to controller 40 by a network connection such as an internet, an intranet, an Ethernet, a wireless network, or the like. Along with programming code, controller 40 may include stored data for implementing the methods described herein, and may generate and/or store data that records perimeters with corresponding to the treatment of one or more patients. Many components of console 14 may be found in or modified from known commercial phacoemulsification systems from Abbott Medical Optics Inc. of Santa Ana, California; Alcon Manufacturing, Ltd. of Ft. Worth, Texas; Bausch and Lomb of Rochester, New York; and other suppliers.

FIG. 2 illustrates a surgical cassette of the present invention, including components of surgical cassette 100. Surgical cassette 100 is an assembly of fluid pathways and connected tubing configured to manage one or more of the following: fluid inflow, fluid outflow, fluid vacuum level, and fluid pressure in a patient's eye E when coupled with console 14. Surgical cassette 100 may include grip loop handle 101, which provides a sterile means for holding and positioning surgical cassette 100 under finger grip control. In an embodiment, grip loop handle 101 is designed for an index finger to pass completely thru the loop of the handle. The grip loop handle 101 may also be designed for the pad of the thumb to rest on outer top surface of grip loop handle 101.

In an embodiment, surgical cassette 100 may include a thumb shield 102. As illustrated in FIG. 2, thumb shield 102 may have a raised border above grip loop handle 101, which is configured and dimensioned to surround a sterile gloved thumb to reduce potential for contact with non-sterile surfaces during insertion of surgical cassette 100 into console. Thumb shield 102 may have one or more surface elements. For example, thumb shield 102 may have one or more generally horizontally extending raised surfaces to constrain the tip of the thumb from extending beyond the upper shielded coverage of the frame of surgical cassette 100. Thumb shield 102 may have in the alternative or in addition to the one or more horizontally extending raised surface, one or more generally vertically extending raised surfaces to constrain the side of the thumb from slipping sideways (left or right) beyond the coverage of the thumb shield 102 constraining surface(s).

In an embodiment, surgical cassette 100 may include drain bag port 103. As illustrated in FIG. 2, drain bag port 103 is an axially extending cylindrical port with a central opening to enable the transfer of fluid from the inside of the surgical cassette 100 manifold to an externally attached collection reservoir such as drain bag or collection vessel 140 (see FIGS. 9a and 9b). In an embodiment as illustrated in FIG. 3, drain bag port 103 may have one or more recessed notches 103a in the end face of drain bag port 103 to provide one or more gaps for fluid to flow into an externally attached bag. Such a feature helps to minimize the potential for the bag surface to obstruct fluid outflow through the port. Inside surface feature 103b may be configured to accept a male slip luer fitting to support the connection to external tubing sets.

As illustrated in FIG. 2, surgical cassette 100 may include a drain bag hook 104. Drain bag hook 104 is a mechanical feature extending outward from the surface of surgical cassette 104 and is configured to interface with a corresponding slot feature in the drain bag 140 (see FIG. 9a) to support the weight of the drain bag as it collects fluid.

Surgical cassette 100 may also include one or more clamping domes 106. As illustrated in FIG. 2, clamping domes 106 may be a raised pattern of spherical domed surfaces with a single high-point to provide low friction wiping contact surfaces during loading and concentrate axial clamping forces in specific zones after loading surgical cassette 100 with console 14. It is also envisioned that the one or more clamping domes 106 may be of any shape or size suitable for its function or desired aesthetic look and feel.

In an embodiment, surgical cassette 100 may include peristaltic pump tube 107. FIG. 4a shows the backside of surgical cassette and peristaltic pump tube 107. Peristaltic pump tube 107 may be an elastomeric length of tubing that is configured to generate positive displacement of fluid flow in the direction of pump roller (not shown) when a portion of the tubing is compressed between the peristaltic pump rollers of console 14 and the backing plate pump profile 108 of the surgical cassette 100. It is also envisioned that any type of flow-based pump and corresponding components may be used with surgical cassette 100. In an embodiment, backing plate pump profile 108 may be comprised of contoured surfaces formed on the inside of cassette frame/front plate 100a to provide a compressing tubing while creating peristaltic pumping flow.

As illustrated in FIGS. 4a, 4b, and 4c, surgical cassette 100 may have axial mating plane surfaces 105. Axial mating plane surfaces 105 are outer border faces of cassette frame/front plate 100a that form a surface mating with console 14 within cassette receiver 123 after loading.

In an embodiment, surgical cassette 100 may also include one or more peristaltic tube form retainers 109. (See FIGS. 4a, 4b, 4c, 5, 6, and 18) Clamping surfaces formed between the cassette frame/front plate 100a and backing plate 100b are configured to axially retain the tubing to maintain consistency of tubing stretch and provide centering of tubing within peristaltic pump profile 108. Form retainers 109 may comprise mating sections 109a of cassette frame front plate 100a. Form retainers 109 are configured and dimensioned to shape peristaltic pump tube 107 and in the embodiment illustrated in the figures, to guide peristaltic pump tube 107 into an approximately 180 degree turn on each end of tube 107.

In an embodiment as illustrated in FIGS. 4a, 4b, and 4c, backing plate 100b may be recessed within cassette frame/front plate 100a such that when surgical cassette 100 is inserted into console 14, backing plate 100b does not touch the cassette receiver 123. In the alternative, backing plate 100b may be configured and dimensioned to touch cassette receiver 123.

Referring to FIGS. 5a, 5b, 6, 7, and 18, surgical cassette 100 may also include one or more pump tube interface ports 110. Pump tube interface ports 110 are inlet and outlet transition ports to transition fluid flow from internal molded manifold fluid flow channels 111 to peristaltic pump tube 107. In an embodiment, surgical cassette 100 may also include one or more manifold fluid flow channels 111. Manifold fluid flow channels 111 are fluid flow pathways formed as raised surfaces allowing fluid to flow in internal channels between the raised surfaces and outer perimeter sealing border of gasket 120 to retain fluid within the manifold fluid flow channels 111 under positive pressure and vacuum conditions. Manifold fluid flow channels 111 may comprise irrigation flow channel 111a, which is a pathway with an inlet tubing port from balance salt solution (BSS) irrigation bottle metered by valves to one or more, preferably two outlet ports: (1) aspiration tubing outlet port 118 connected to an external surgical handpiece 12 flowing fluid to the eye, which may be metered or controlled by irrigation valve 113; and (2) venting line 111b providing BSS irrigation fluid into an aspiration line of flexible conduits 18 which may be metered or controlled by vent valve 114.

Manifold fluid flow channels 111 may also have aspiration flow channel 111b. Aspiration flow channel 111b may include a pressure/vacuum sensor element 111c, a pumping outlet port 111d, and two inlet ports comprising aspiration fluid inflow from tubing line connected to external surgical handpiece 12 and venting fluid inflow from BSS irrigation bottle, which may be metered by vent valve 114. Manifold fluid flow channels 111 may also comprise vent flow channel 111c. Vent flow channel 111c is a pathway configured to provide BSS irrigation fluid into the aspiration line, which may be metered by vent valve 114 to reduce vacuum level in the aspiration line following handpiece 12 tip obstruction or occlusion. Manifold fluid flow channels 111 may also have manifold channel sealing surfaces 112, which comprise the top surface or portion thereof of the channels 111.

Referring to FIGS. 4a, 4b, 4c, 5, and 6, surgical cassette 100 may include irrigation valve 113, which in an embodiment may have a dome-like shape. Irrigation valve 113 may be an elastomeric deformable surface which allows irrigation flow from a BSS bottle to external surgical handpiece 12 when uncompressed and shuts off flow when deformed inwards towards manifold fluid flow channels 111. Surgical cassette 100 may also include vent valve 114, which in an embodiment may have a dome-like shape. Vent valve 114 may be an elastomeric deformable surface which allows irrigation flow from the BSS bottle through the aspiration line that coupled with the external surgical handpiece 12 resulting in vacuum level reduction when uncompressed and shuts off flow when deformed inwards towards manifold fluid flow channels 111. The level of fluid flow may be controlled based upon the level of compression of valves (113 and 114)—from full flow to intermediate flow to no flow.

In an embodiment illustrated in FIGS. 5a, 5b, and 6, surgical cassette 100 may have irrigation valve control surface 115. Irrigation valve control surface 115 may be a raised sealing surface in manifold fluid flow channels 111 that provides irrigation fluid flow reduction or shutoff from the BSS irrigation bottle to an irrigation inlet fitting of surgical handpiece 12 when irrigation valve control dome is compressed or activated. Surgical handpiece 100 may also include vent valve control surface 116. Vent valve control surface 116 may be a raised sealing surface in manifold fluid flow channels 111 that provides shutoff of venting of irrigation fluid flow from the BSS irrigation bottle to an aspiration fitting of surgical handpiece 12 when vent valve 114 is compressed or activated.

In an embodiment illustrated in FIG. 8, surgical cassette 100 may include irrigation inlet tubing port 117, aspiration outlet tubing port 118, and irrigation outlet tubing port 119. Irrigation inlet tubing port 117 may be a connection port for tubing extending to the BSS irrigation bottle to deliver irrigation fluid to manifold fluid flow channels 111. Aspiration outlet tubing port 118 may be a connection port for tubing extending to the surgical handpiece 12 irrigation fitting to deliver irrigation fluid from manifold fluid flow channels 111 to patient's eye E. Irrigation outlet tubing port 119 may be a connection port for tubing extending to the surgical handpiece 12 aspiration fitting for removing fluid from a patient's eye E by means of a pump, such as a flow-based pump, preferably a peristaltic pump comprising the peristaltic pump tube 107. In an embodiment, surgical cassette 100 may also include or in the alternative of drain bag port 103, optional drain port 103c, which may be connected to an external tubing line or reservoir. In an embodiment, drain port 103c may be closed by a plug or similar device known in the art.

Figure 10B:
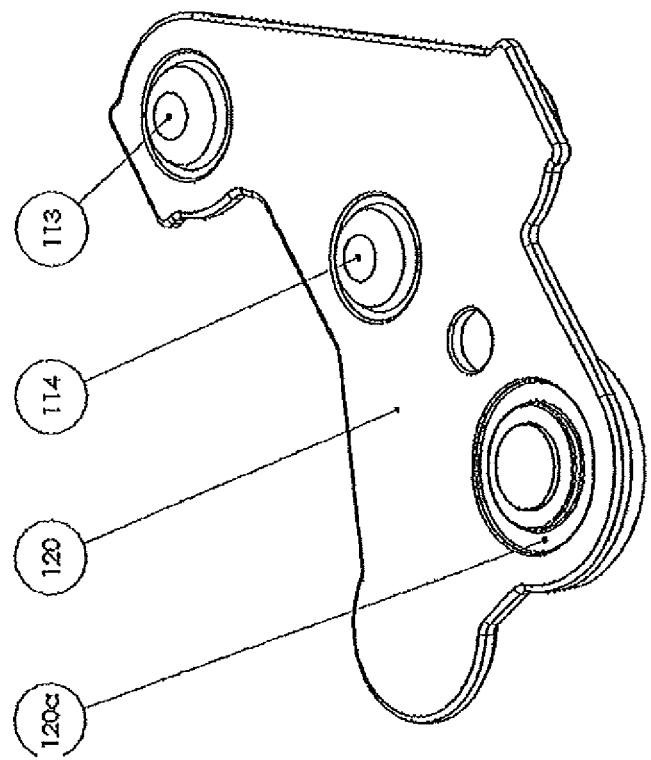
FIG. 10*b* is a perspective view of the front of an exemplary gasket.
Figure 10A:
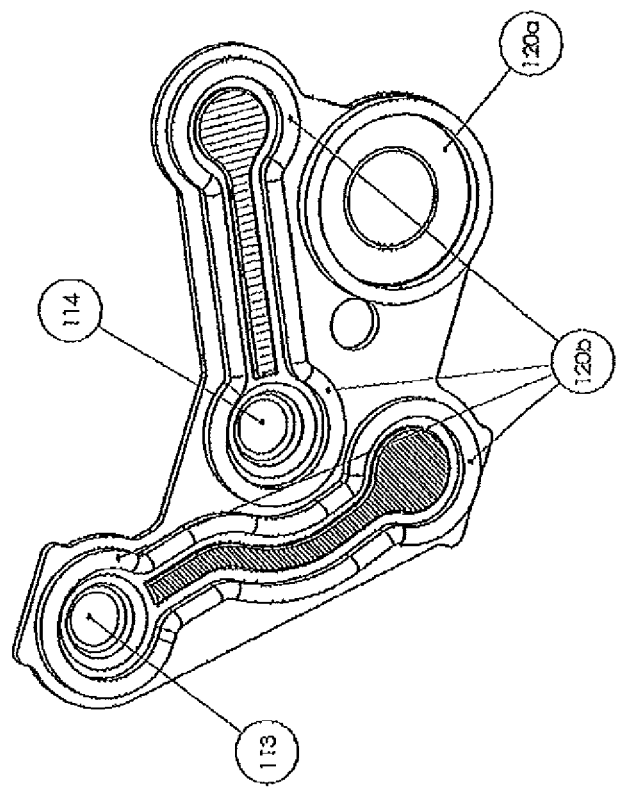
FIG. 10*a* is a perspective view of the back of an exemplary gasket.
Figure 13:
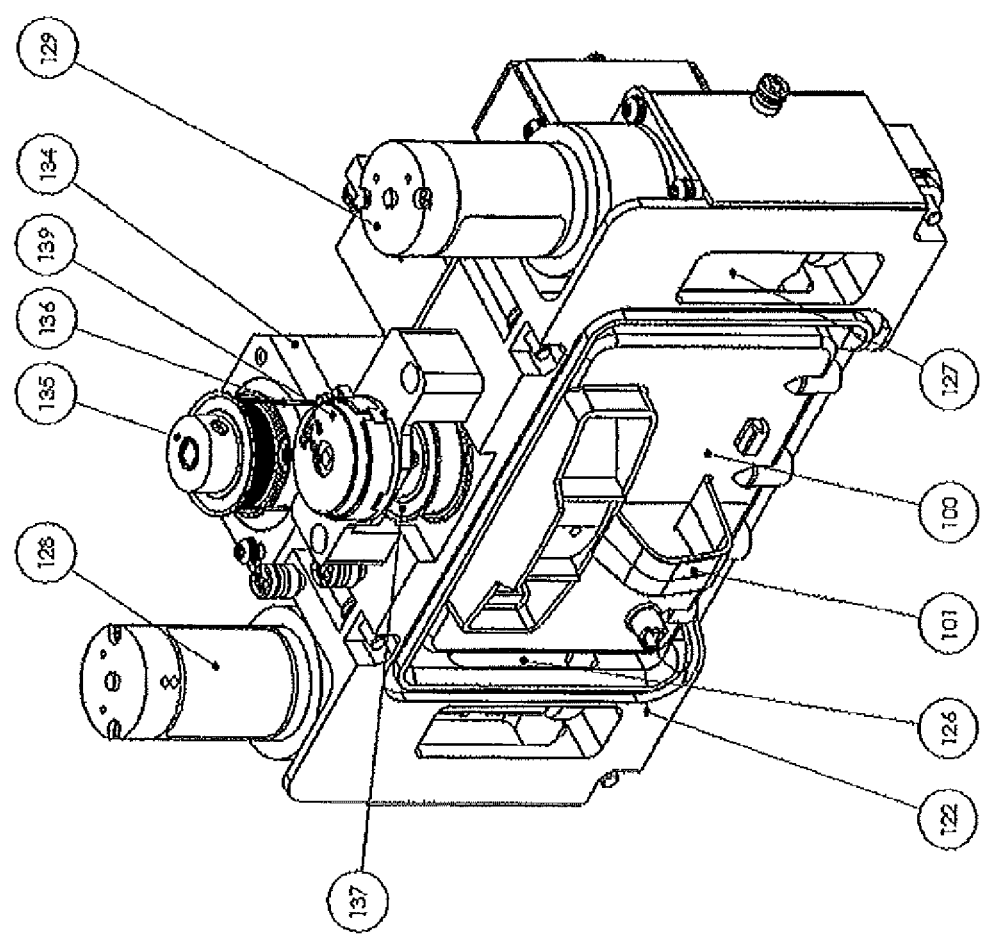
FIG. 13 is a perspective view of an exemplary surgical console with a surgical cassette coupled therewith.
Figure 14A:
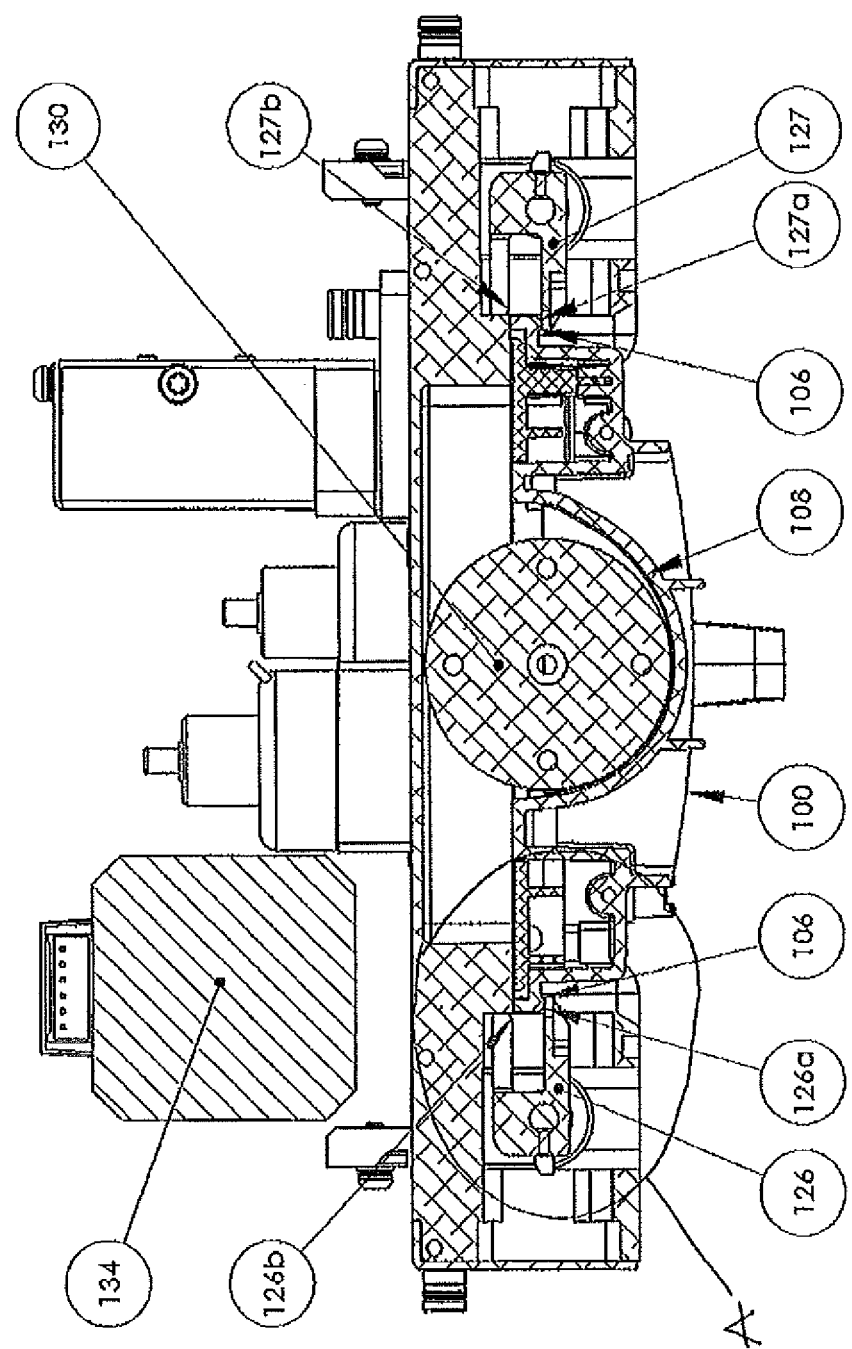
FIG. 14*a* is a cross-sectional view of an exemplary surgical cassette clamping mechanism.
Figure 14B:
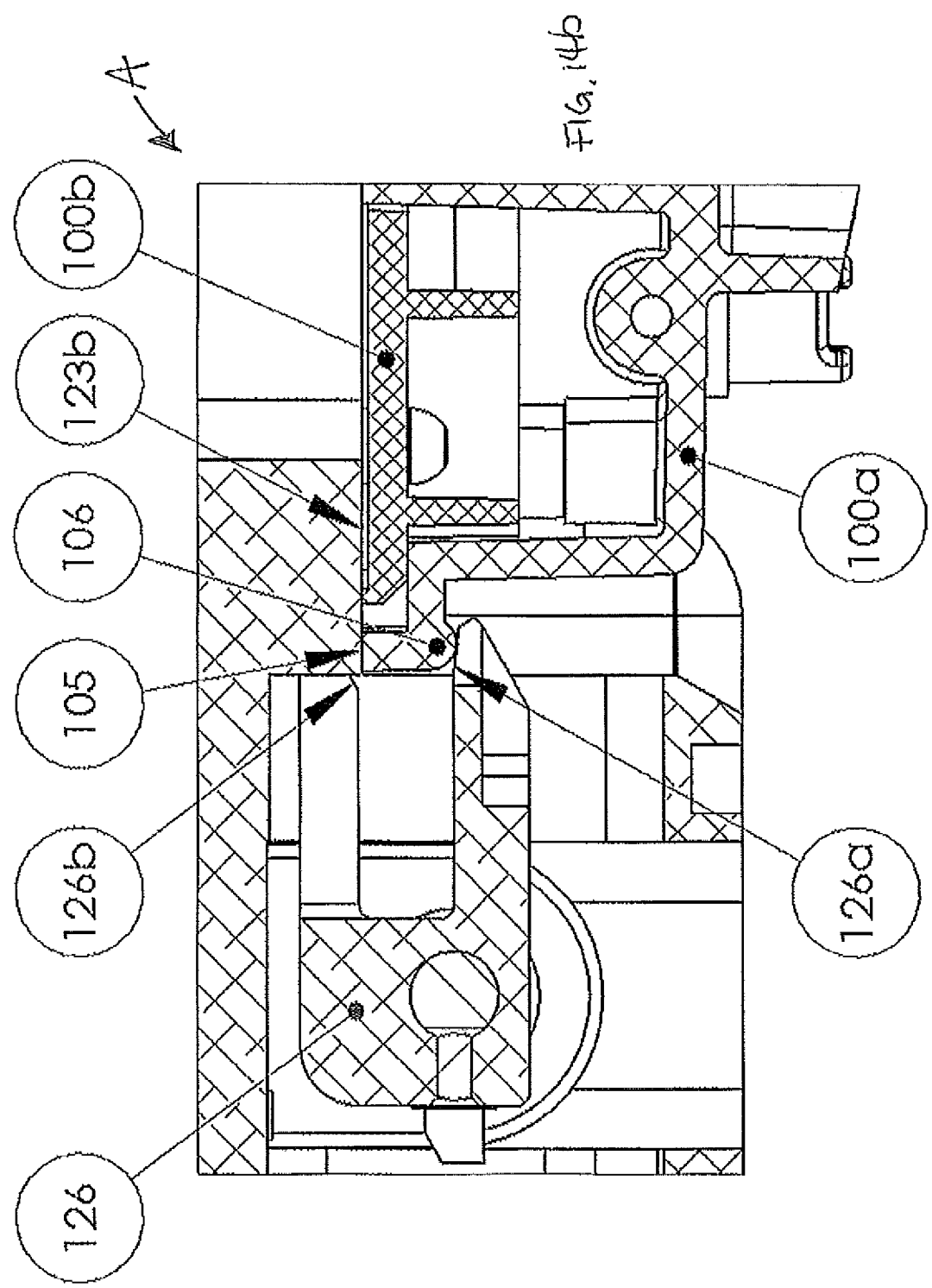
FIG. 14*b* detailed view of the exemplary surgical cassette interface (part A) as illustrated in FIG. 14*a*.

Surgical cassette 100 may include gasket 120 as illustrated in FIGS. 10a and 10b, which may be an integrated elastomeric fluid channel sealing gasket. Gasket 120 may include a vacuum/pressure sensor diaphragm 120a, irrigation valve control dome 113, and vent valve control dome 113. Gasket 120 may also include fluid channel sealing surfaces 120b. Vacuum/pressure sensor diaphragm 120a may be a sealed flexible annular membrane with a central magnetic coupling disk which deforms: (1) proportionally outwards under fluid pressure conditions compressing a magnetically-coupled force displacement transducer of console 14 allowing for non-fluid contact measurement of fluid pressure level inside the aspiration fluid pathways of surgical cassette 100; and (2) proportionally inwards under fluid vacuum conditions extending the magnetically-coupled force displacement transducer of console 14 allowing for non-fluid contact measurement of fluid vacuum level inside the aspiration fluid pathways of surgical cassette 100. In an embodiment, gasket 120 may have one or more fluid channel sealing surfaces 120d, which may be a raised lip portion of the gasket 120. In the embodiment shown in FIG. 10a, two such sealing surfaces 120b are illustrated.

In an embodiment, gasket 120 may be molded onto the backing plate 100b by co-molding or any other process known in the art. Co-molding the gasket 120 and backing plate 100b result in a combination of elastomeric features of gasket 120 and rigid features of backing plate 100b.

In an embodiment, surgical cassette 100 may also include pressure/vacuum sensor concentric alignment ring 121 as illustrated in FIGS. 4a, 4b, 4c, and 5a. Alignment ring 121 may include a pattern of a radially oriented rib features defining a circular arc of a specific diameter and location to provide for concentric alignment between the center of the magnetically-coupled force displacement transducer 131 of console 14 and the center of vacuum/pressure diaphragm 120a of surgical cassette 100. The pattern may comprise one or more radially oriented rib features, preferably a minimum of three radially oriented rib features.

Figure 16A:
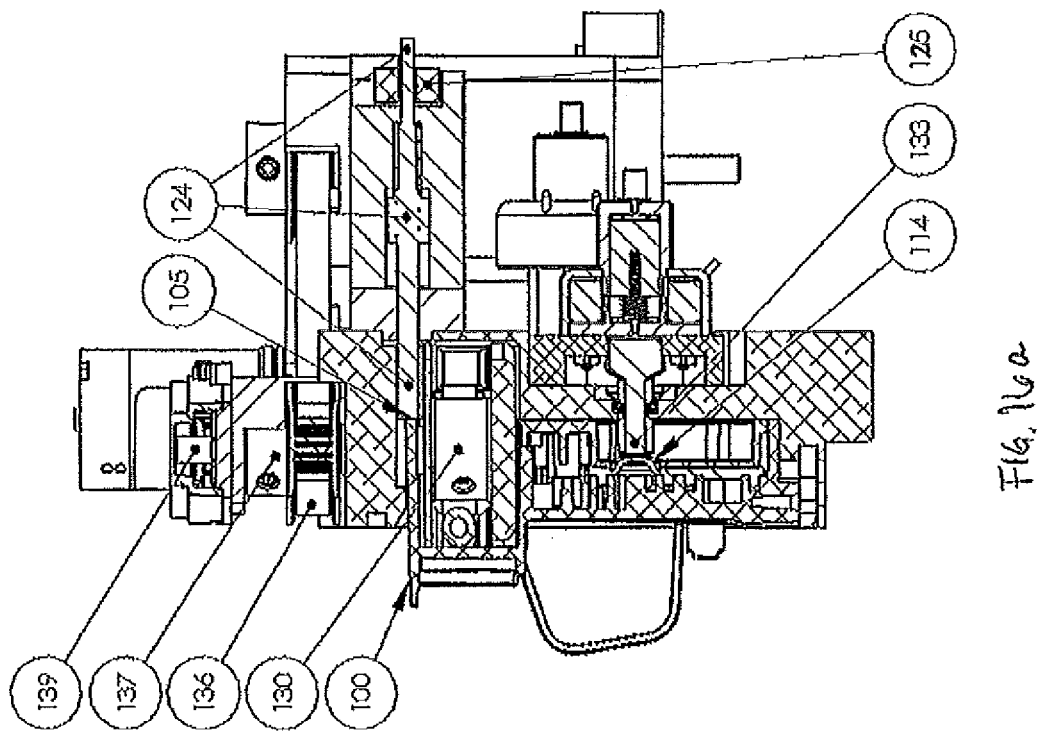
FIG. 16*a* is a cross-sectional view of an exemplary surgical cassette detection mechanism.

In FIGS.: 11, 11a, 12 and 13, fluidics module 122 is illustrated according to an embodiment of the present invention. Fluidics module 122 comprises an assembly of components mounted in console 14 for interfacing with surgical cassette 100. Fluidics module 122 may have one or more of the components described herein. Fluidics module 122 may have cassette receiver 123, cassette pre-load detection pin 124, and pre-load detection switch 125 (shown in FIG. 16a). Cassette receiver 123 may be a section of fluidics module 122 defining an engagement area for loading and aligning surgical cassette 100 in its intended position relative to various components of fluidics module 122. Cassette receiver 123 may have tapered lead-in pre-alignment surfaces 123a, which may include outside vertical and horizontal border surfaces of cassette receiver 123 that may be tapered towards the center of the opening of cassette receiver 123 to guide surgical cassette 100 into a substantially centered position during off-angle insertion. Cassette receiver 123 may also have axial interface surface 123b, which may include planar engagement surfaces where cassette frame/front plate 100a bottoms out when fully constrained by rotary clamps 126, 127.

Figure 15B:
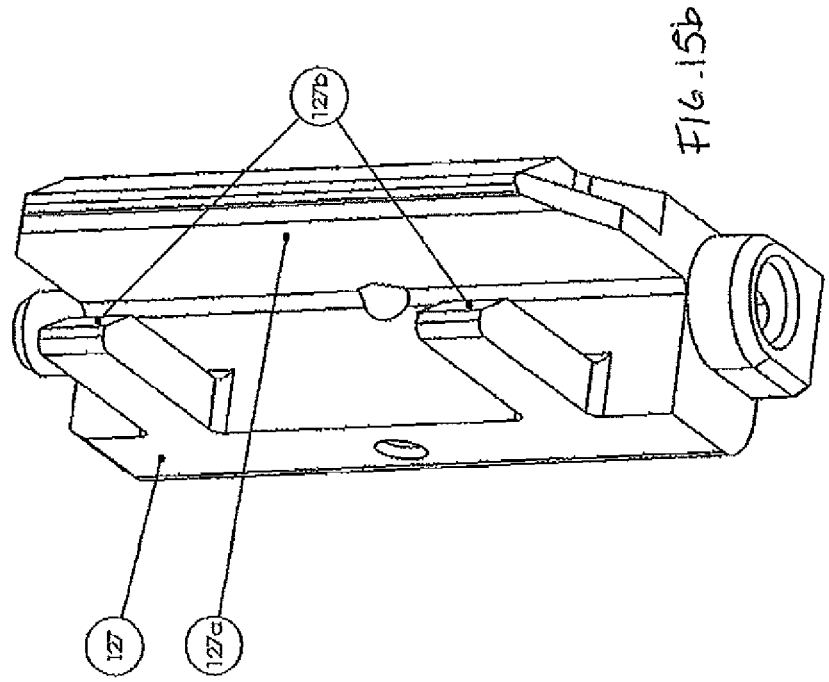
FIG. 15*b* is a perspective view of an exemplary surgical cassette clamp.
Figure 15A:
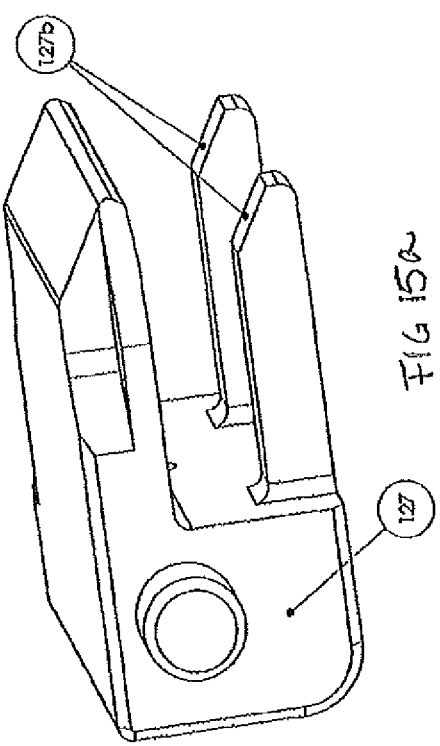
FIG. 15*a* is a perspective view of an exemplary surgical cassette clamp.
Figure 17A:
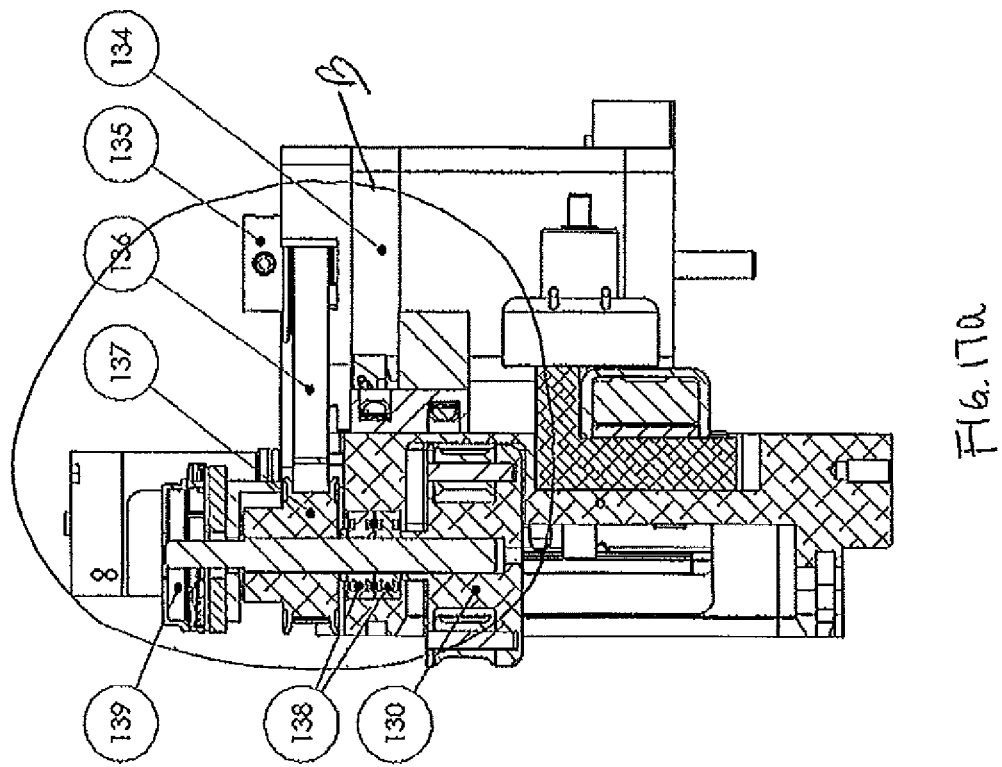
FIG. 17*a* is a cross-section view of an exemplary peristaltic pump roller assembly.
Figure 16B:
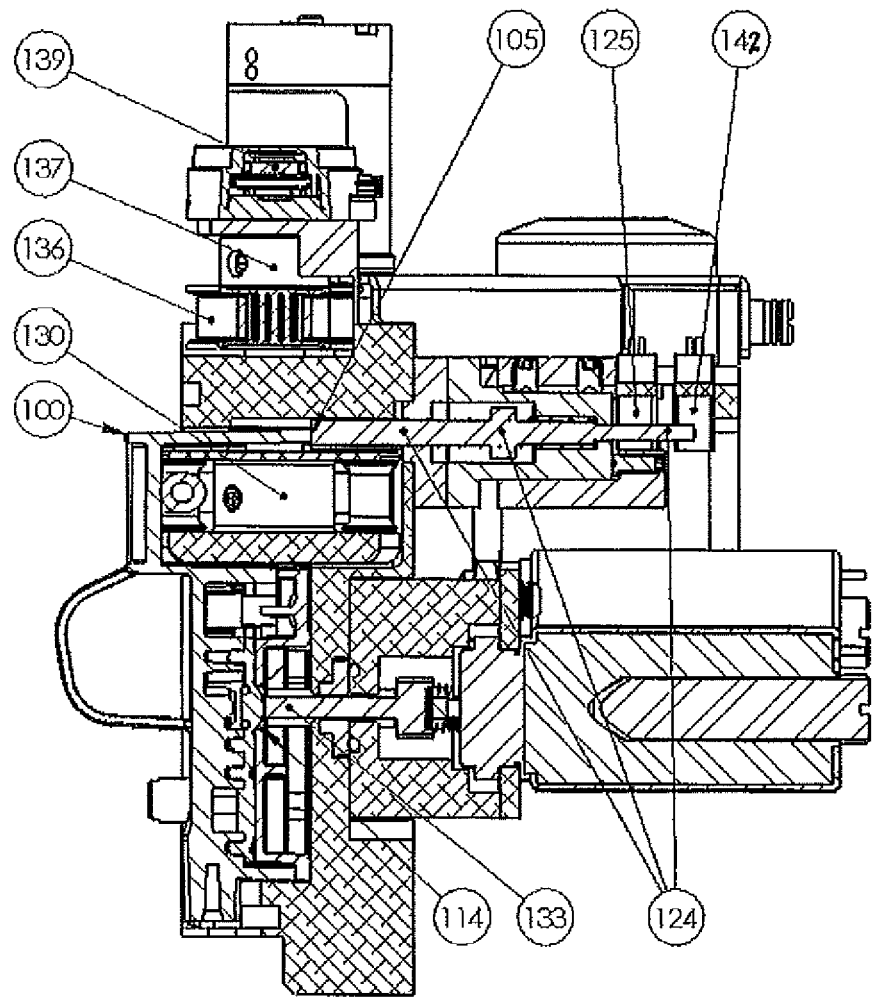
FIG. 16*b* is a cross-sectional view of an exemplary surgical cassette detection mechanism.

Cassette pre-load detection pin 124 may be a spring-loaded pin displaced rearwards when surgical cassette 100 is initially inserted with an end or side surface triggering a switch and initiating closure of rotary clamps 126, 127. Pre-load detection switch 125 may be a switch component that changes electrical output state when cassette pre-load detection pin 124 has been displaced to a specific axial position indicating surgical cassette 100 is in an appropriate position for loading engagement by rotary clamps 126, 127 (see FIGS. 15a and 15b). In an optional embodiment, as shown in FIG. 16b, a second detection switch 142 may be located next to or behind detection switch 125 to monitor the position of pre-load detection pin 124 to verify that surgical cassette 100 reaches its intended interface position at the completion of the cassette clamping mechanism closure.

Left rotary clamp 126 may be a rotating clamping component configured with specific surfaces to clamp surgical cassette 100 when rotated in a counter-clockwise direction as viewed from the top T and specific ejection surfaces to disengage surgical cassette 100 when rotated in the opposite direction. Right rotary clamp 127 may be a rotating clamping component configured with specific surfaces to clamp surgical cassette 100 when rotated in a clockwise direction as viewed from top T and specific ejection surfaces to disengage surgical cassette 100 when rotated in the opposite direction.

In an embodiment, fluidics module 122 may have a left clamping motor actuator 128 and a right clamping motor actuator 129. Left clamping motor actuator 128 may be a reversible rotary actuator powered by electricity, pneumatics, hydraulics, or any other means know in the art, that controls the rotational position of the left rotary clamp 126 to alternately load and eject surgical cassette 100. Right clamping motor actuator 129 may be a reversible rotary actuator powered by electricity, pneumatics, hydraulics, or any other means know in the art, that controls the rotational position of the right rotary clamp 127 to alternately load and eject surgical cassette 100. The actuation of the motor actuators 128 and 129 may be simultaneously or individually controlled.

In an embodiment, fluidics module 122 may have a pump roller assembly 130. Pump roller assembly may have a configuration of multiple roller elements in a circular or substantially circular pattern which produce peristaltic flow-based fluid transport when rotated against compressed fluid-filled peristaltic pump tube 107.

In an embodiment, fluidics module 122 may have a force displacement transducer 131. Force displacement transducer 131 may operate by means of a magnetic coupling, such that fluid vacuum inside manifold fluid flow channels 111 causes deformation inwards of vacuum/pressure sensor diaphragm 120a in surgical cassette 100, which axially extends force displacement transducer 131 resulting in a change of an electrical output signal in proportion to a vacuum level. Positive fluid pressure in manifold fluid flow channels 111 results in an outward extension of vacuum/pressure sensor diaphragm 120a and compression of the force displacement transducer 131.

In an embodiment, fluidics module 122 may have irrigation valve plunger 132 and vent valve plunger 133. Irrigation valve plunger 132 may have an axial extension of the plunger that compresses irrigation valve 113 of surgical cassette 100 resulting in a decrease or shutoff of irrigation flow to external irrigation tubing line of flexible conduit 18. Irrigation valve plunger 132 may also operate by a spring-loaded retraction of the plunger to allow varying levels of irrigation flow. Vent valve plunger 133 may have an axial extension of the plunger that compresses vent valve 114 of surgical cassette 100 resulting in a decrease or shutoff of irrigation venting flow to external aspiration tubing line of flexible conduit 18. Vent valve plunger 133 may also operate by a spring-loaded retraction of the plunger to allow irrigation pressure fluid flow to vent vacuum level in aspiration tubing line of flexible conduit 18.

In an embodiment, fluidics module 122 may have one or more of the following components: peristaltic drive motor actuator 134, peristaltic pump motor drive pulley 135, peristaltic drive belt 136, peristaltic roller driven pulley 137, and pump roller guide bearings 138. Peristaltic drive motor actuator 134 may be a reversible rotary actuator powered by electricity, pneumatics, hydraulics, or any other means known in the art that controls the rotational position of the peristaltic pump roller assembly 130. Peristaltic pump motor drive pulley 135 may have a pulley wheel connected to the rotary drive shaft of peristaltic drive motor actuator 134 to provide a mating interface for peristaltic drive belt 136 when peristaltic drive motor actuator 134 is oriented on an offset parallel axis to peristaltic pump roller assembly 130 for reducing overall height of fluidics module 122. Peristaltic roller driven pulley 137 may have a pulley wheel connected to rotary shaft peristaltic pump roller assembly 130. Peristaltic drive belt 136 may be a belt connecting peristaltic pump motor drive pulley 135 to peristaltic roller driven pulley 137 to transfer rotation of the pump drive motor shaft to the peristaltic pump roller assembly 130.

Pump roller guide bearings 138 may have at least one low friction bearing placed in concentric alignment with peristaltic pump roller assembly 130 to guide shaft rotation of peristaltic pump roller assembly 130. Pump roller guide bearings 138 may compensate for off-axis forces from compression of peristaltic pump tube 107 by peristaltic pump roller assembly 130 and peristaltic drive belt 136 tension between pulleys 135 and 137.

In an embodiment, fluidics module 122 may have rotary pump roller position encoder 139. Rotary pump roller position encoder may have an electronic output signal indicating rotary position of peristaltic pump roller assembly 130, which may be used to derive and confirm intended rotational speed during peristaltic pumping. Rotary pump roller position encoder 139 may also be used to provide controlled rotary position changes for the following purposes: increase or decrease pressure level in fluid line by a target amount by transferring a pre-determined volume of fluid into or out of the fluid line faster than closed-loop pressure monitoring allows based on an algorithm assuming a known overall system volume; and/or increase or decrease vacuum level in fluid line by a target amount by transferring a pre-determined volume of fluid into or out of fluid line faster than closed-loop vacuum monitoring allows based on an algorithm assuming a known overall system volume.

Figure 19:
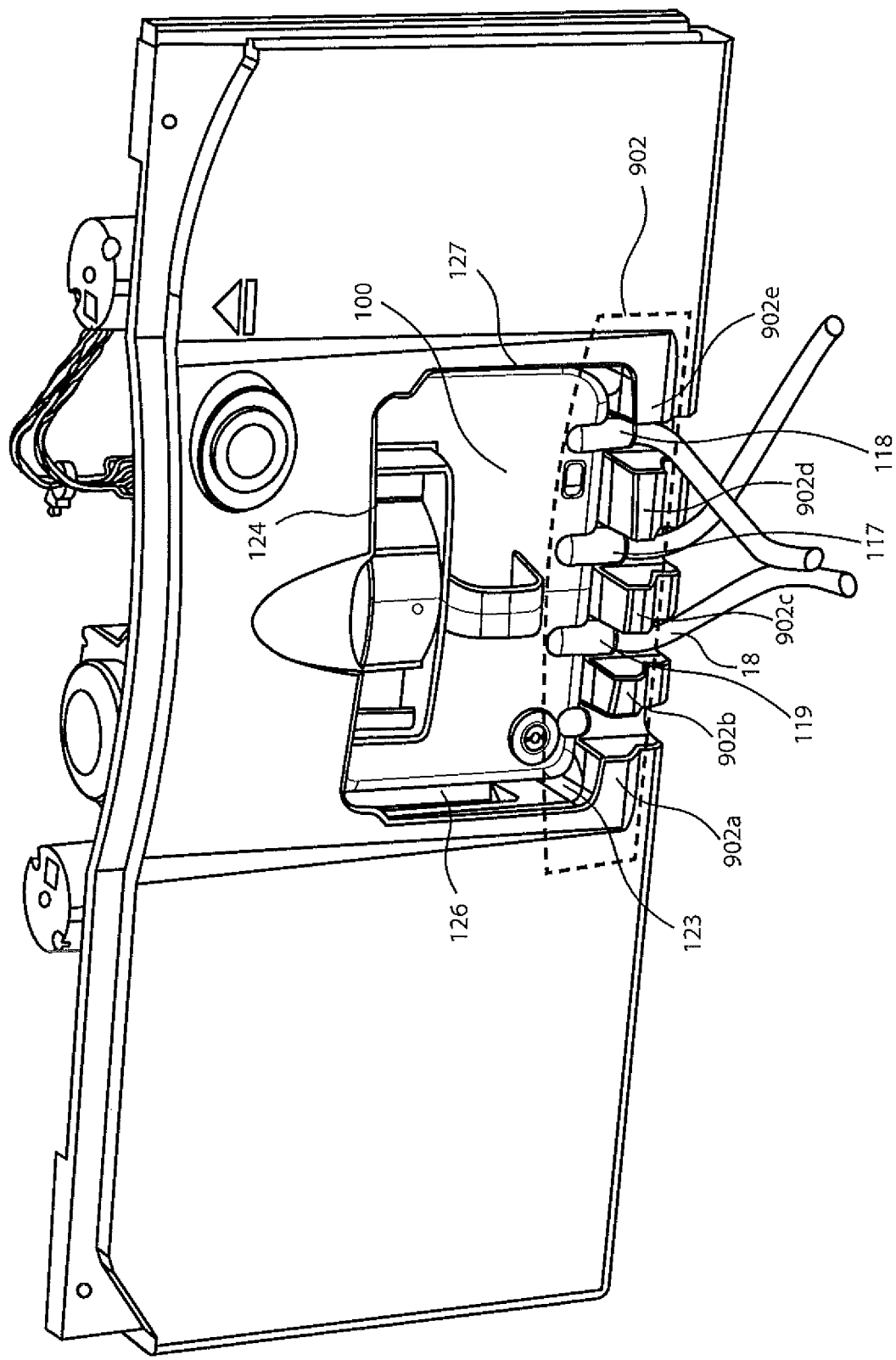
FIG. 19 is a perspective view illustrating a surgical console having a pre-alignment feature.

FIG. 19 is an illustration of an exemplary embodiment having a pre-alignment feature 902 for aiding in the alignment of cassette 100 for insertion into cassette receiver 123 (shown in FIG. 20) on the console. In the illustration, the pre-alignment feature 902 comprises a shelf having multiple shelf components 902a, 902b, 902c, 902d, 902e extending outward beyond the plane formed by the cassette receiver 123 at the face of the console. The multiple components of feature 902 may allow for guidance of cassette 100 into cassette receiver 123, and the simultaneous guidance of administrative tubing 18 such as may be correspondent to at least irrigation inlet tubing port 117, aspiration outlet tubing port 118, and irrigation outlet tubing port 119 of cassette 100 into the slots formed between shelf components 902b and 902c, and between components 902c and 902d, and between components 902d and 902e. Pre-alignment feature 902 may be provided in conjunction with secondary pre-alignment aspects, such as the tapered lead-in pre-alignment surfaces 123a referenced above, which may guide the cassette 100 to be centered in the opening of cassette receiver 123. By way of non-limiting example, such pre-alignment surfaces 123a may comprise an extension of the profile of the cassette 100 geometry, such as in the upper right and left hand corners of the cassette receiver 123, to serve as the secondary pre-alignment aspect.

Upon proper alignment of cassette 100 with feature 902, and of tubing 18 into slots formed by shelf components 902a, 902b, 902c, 902d, 902e, the cassette may be detected in cassette receiver 123, such as by cassette pre-load detection pins 124. Once a properly aligned cassette 100 is detected, the cassette may be affirmatively received into cassette receiver 123, such as by actuation of left and right rotary clamps 126, 127.

As such, pre-alignment feature 902 may provide an additional guiding element for facilitating the proper loading of cassette 100 into the cassette receiver 123 associated with the surgical console. The pre-alignment feature 902 may be formed as a protruding area along the lower edge of the cassette receiver 123 by any known method, and may be integral to, or separately formed from, the front face of the console. The feature 902 may be, for example, molded plastic formed integrally with the console, or may be glued onto or otherwise attached to the face of the console. Thus, feature 902 may be molded, machined, or otherwise fabricated by suitable means understood to those skilled in the pertinent arts. The distance by which the feature 902 extends outwardly from the console may vary for different features 902, or may vary as between feature components 902a, 902b, 902c, 902d, 902e within a single feature 902. Additionally, the extension distance outward may vary along the length of each individual component 902a, 902b, 902c, 902d, 902e.

The pre-alignment feature may have a semicircular, rectangular, or triangular cross-sectional shape, and the slots formed by feature components 902a, 902b, 902c, 902d, 902e are provided vertically from the upper portion to the lower portion of feature 902 and may be of semicircular, rectangular, or triangular shape. As referenced, the slots may receive administrative tubing 18, or the slots may receive, or partially receive, irrigation inlet tubing port 117, aspiration outlet tubing port 118, or irrigation outlet tubing port 119, by way of non-limiting example. Thereby, the slots may further aid in the alignment of cassette 100 into cassette receiver 123.

Accordingly, in addition to providing pre-alignment for the cassette 100 and for the administrative tubing 18, the pre-alignment feature may also provide a support shelf on which at least a portion of the surgical cassette 100 may rest during insertion to and ejection from the cassette receiver 123. More particularly, if, for example, the surgical cassette 100 is ejected from the cassette receiver 123 outside of the immediate physical control of a user, the surgical cassette 100 may rest on the support shelf provided by the pre-alignment feature 902 such that the surgical cassette 100 is precluded from falling to the floor of the surgical room. The support shelf provided by feature 902 may also allow for the hands-free inspection of the surgical cassette 100 by a user prior to insertion into the cassette receiver 123. As such, the upper portion of feature 902, and/or one or more of feature components 902a, 902b, 902c, 902d, 902e may have physically associated therewith a high friction surface for retaining the lower portion of cassette 100. Such a high friction surface may be, for example, rubber, or an uneven and/or roughed surface.

Operation of Surgical Cassette and Console

The following describes an example of operating surgical cassette 100 and console 14 according to an embodiment of the present invention. A surgical technician grasps surgical cassette 100 by placing an index finger through the opening of grip loop handle 101 and gripping handle 101 with thumb pressure on thumb shield 102 (outer top surface of handle). The surgical technician's hand can remain sterile while tubing lines are handed off to supporting non-sterile staff to make connections to the non-sterile BSS irrigation bottle. With the surgical technician's thumb being shielded from inadvertent contact with non-sterile outer surfaces of console 14 by means of thumb shield 102, surgical cassette 100 may be directly inserted into cassette receiver 123 of fluidics module 122 with centering guidance provided by tapered outer surfaces 123a. The direct axial insertion of surgical cassette 100 into cassette receiver 123 of fluidics module 122 results in axial mating plane surfaces 105 contacting ejection surfaces 126b and 127b of left and right rotary clamps 126,127. (See FIGS. 14a, 14b, 15a, and 15b).

Approximately synchronized with contacting ejection surfaces 126b and 127b of rotary clamps 126, 127, cassette pre-load detection pin 124 is compressed triggering a switch signal to be sent from cassette pre-load detection switch 125 to the control means of console 14. Triggering of cassette pre-load detection switch 125, triggers rotation of clamping motor actuators 128, 129 and contact between loading clamp surfaces 126a, 127a of rotary clamps 126, 127 and clamping domes 106 on cassette frame/front plate 100a. Clamping motor actuators 128, 129 will continue to rotate until axial mating plane surfaces 105 of cassette frame/front plate 100a are compressed fully flat and parallel to mounting reference surfaces of fluidic module 122.

Surgical cassette 100 is guided into horizontal and vertical preferred alignment by concentric alignment of ribs 121 of pressure/vacuum sensor diaphragm 120a of surgical cassette 100 with outer ring surface 131a (see FIG. 11a) of force displacement transducer 131. See FIG. 11a. After tubing connections are made to external accessories (e.g., handpiece 12 with attached phaco needle tip and irrigation sleeve (not shown)), surgical staff initiates a fluid priming of tubing lines and internal cassette fluid pathways (i.e. manifold fluid flow channels 111) with irrigation fluid delivered from an irrigation source (e.g. BSS bottle).

Figure 20:
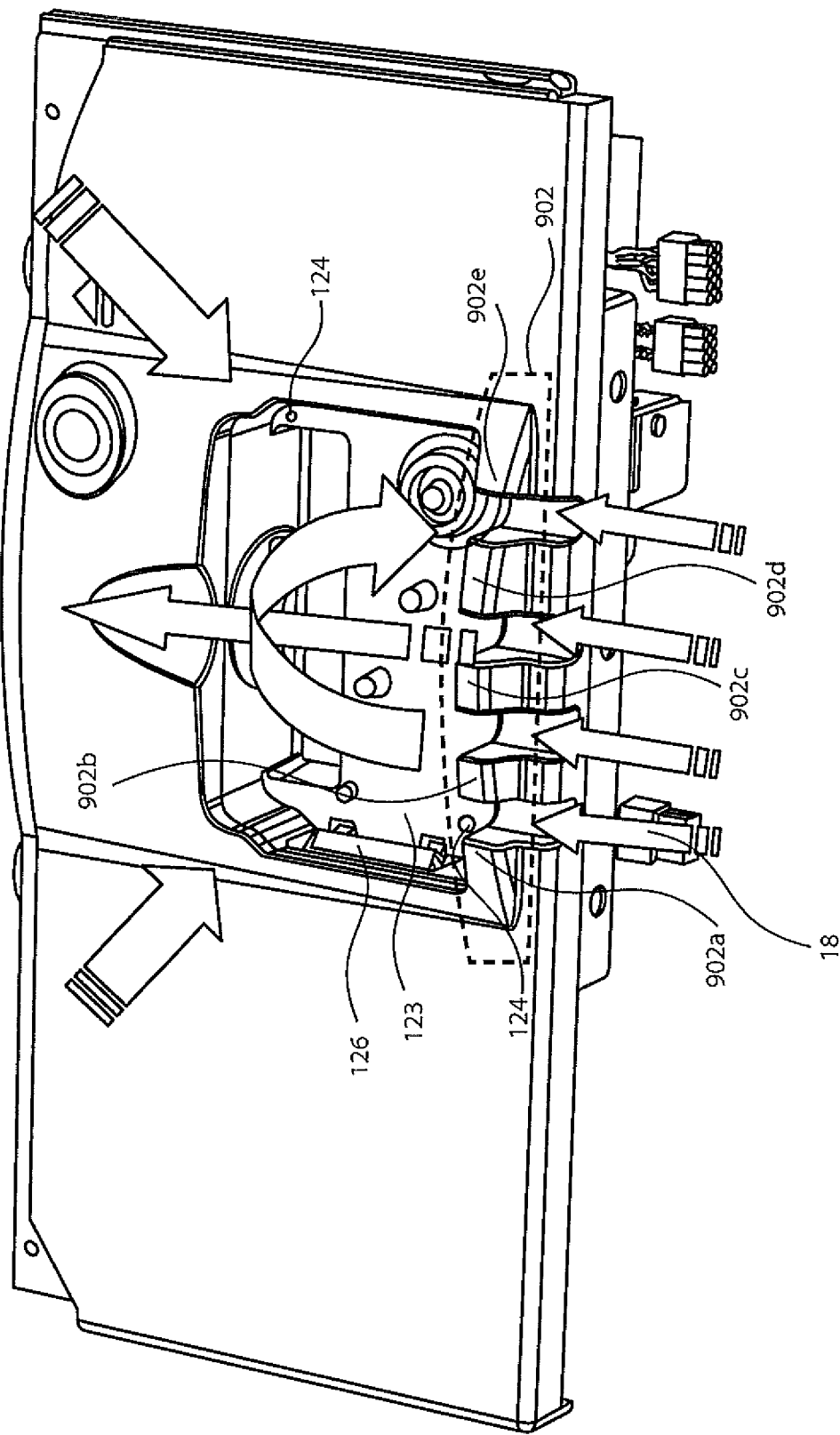
FIG. 20 is a perspective view illustrating the insertion of a surgical cassette into a surgical console using a pre-alignment feature.

In an additional embodiment shown in FIG. 20 and employing, for example, the pre-alignment shelf feature 902 of FIG. 19, the cassette 100 may initially have a lower portion thereof aligned with the uppermost portion of feature 902, and/or may have at least tubing 18 associated with irrigation inlet tubing port 117, aspiration outlet tubing port 118, and irrigation outlet tubing port 119 (see FIG. 19) aligned with the slots formed between feature components 902a, 902b, 902c, 902d, 902e. Once this alignment is achieved, the top portion of cassette 100 may be rotated toward the upper portion of the cassette receiver 123 about an axis running laterally along the contact points between the pre-alignment feature 902 and the bottom portion of the cassette. If this rotation occurs subject to a proper alignment of the cassette 100 along shelf feature 902, the cassette will be received fully into cassette receiver 123 by clamps 126, 127.

Moreover, in certain exemplary embodiments cassette 100 need not be rotated to be inserted into the cassette receiver 123. That is, cassette 100 may be placed directly into the cassette receiver 123, such as using pre-alignment feature 902 as an insertion guide.

Console 14 may verify one or more of the following: proper tubing connections, fluid line sealing, and fluid control operation during the priming procedure by generating flow through aspiration pathways of manifold fluid flow channels 111 by rotating peristaltic pump roller assembly 130 against outer surface of peristaltic pump tube 107 in compression against peristaltic pump profile 108 of backing plate 100b.

Desired and/or appropriate pressure and vacuum levels are verified by means of the magnetically-coupled pressure/vacuum sensor diaphragm 120 pulling outwards on force displacement transducer 131 in proportion to an actual vacuum level and pushing inwards in proportion to actual pressure levels.

Fluid flow may be metered on and off or varied by means of extending and retracting irrigation and vent valve plungers 132, 133, which shutoff or vary fluid flow when extended to compress sealing surfaces of irrigation valve 113 and vent valve 114 against irrigation and vent valve surfaces 115, 116.

A surgical user may control the outflow rate of fluid from externally attached tubing accessories (e.g., handpiece 12 with attached phaco tip and irrigation sleeve (not shown)) by selecting desired aspiration pump flow rate which is converted by one or more control algorithms of console 14 into speed of rotation of peristaltic pump roller assembly 130.

According to an embodiment, to enable reduced overall height of fluidics module 122, peristaltic drive motor actuator 134 may be configured as a parallel axis drive mechanism such as the belt drive and pulley mechanism described herein. In another embodiment, peristaltic drive motor actuator 134 may be oriented such that the drive shaft is perpendicular to the peristaltic pump roller assembly 130 using one or more gears to couple the peristaltic drive motor actuator 134 with the peristaltic pump roller assembly 130. This in turn would also enable a reduction of overall height of fluidics module 122.

Referring to FIGS. 16a, 16b, 17a, and 17b, in another embodiment, using a non-axial drive connection between peristaltic drive motor actuator 134 and peristaltic pump roller assembly 130, a rotary pump roller position encoder 139, which may be any type of indicator known in the art, may be mounted onto the rotating shaft of peristaltic pump roller assembly 130 to detect slippage or asynchronous rotation of peristaltic drive motor actuator 134 with respect to peristaltic pump roller assembly 130. Since peristaltic pumping is generated in direct proportion to peristaltic pump roller assembly 130 to rotational speed of peristaltic drive motor actuator 134 during slippage conditions, placement of rotary pump roller position encoder 139 onto peristaltic pump roller assembly 130 provides increased accuracy and reliability of intended operation.

When the surgical procedure is completed, surgical staff initiate ejection of surgical cassette 100 from fluidics module 122 by activating ejection switch 141 (see FIG. 11a) which signals the clamp motor actuators 128, 129 to reverse rotation and disengage axial mating plane surfaces 105 of surgical cassette 100 from axial interface surface 123b of fluidics module 122 by a controlled distance.

In an embodiment, the final ejected position of surgical cassette 100 results in surgical cassette 100 still being retained on its outer border edges within the lead-in portion 123a (see FIGS. 11 and 11a) of cassette receiver 123 to prevent surgical cassette 100 having internal surgical waste fluid from falling onto the floor.

All references cited herein are hereby incorporated by reference in their entirety including any references cited therein.

Although the present invention has been described in terms of specific embodiments, changes and modifications can be carried out without departing from the scope of the invention which is intended to be limited only by the scope of the claims.

What is claimed is:

1. A method of receiving a cassette to a console of a phacoemulsification system, comprising:
   receiving a bottom portion of the cassette upon a pre-alignment feature adjacent to a lower portion of a cassette receiver of the console; and receiving a top portion of the cassette into an upper portion of the cassette receiver upon rotation of the top portion of the cassette into the upper portion of the cassette receiver about an axis extending at least partially between, and intersecting, contact points between the cassette and the pre-alignment feature, wherein the pre-alignment feature comprises a support shelf, including multiple shelf components, extending in a longitudinal direction and defining a plurality of slots spaced from each other in the longitudinal direction, the plurality of slots extending vertically to a receiving space from the lower portion;

wherein the support shelf is configured with a surface to support at least a portion of the cassette as the cassette receiver receives at least one of the bottom portion and the top portion of the cassette, wherein the surface is configured with a surface to retain the lower portion of the cassette.

2. The method of claim 1, further comprising clamping the cassette into the cassette receiver following an aligned receiving of the bottom portion and an aligned receiving of the top portion.

3. The method of claim 1, further comprising ejecting the cassette after use following said receiving steps, wherein the cassette rests at least partially on the pre-alignment feature following said ejecting.

4. The method of claim 1, further comprising rejecting the cassette by the cassette receiver if the cassette is misaligned during either of said receiving steps.

5. The method of claim 4, wherein the cassette rests at least partially on the pre-alignment feature following said rejecting.

6. The method of claim 4, further comprising clamping the cassette into the cassette receiver responsively to actuation of at least one alignment detection pin.

7. A method of receiving a cassette to a console of a phacoemulsification system, comprising:

receiving a bottom portion of the cassette upon a pre-alignment feature adjacent to a lower portion of a cassette receiver of the console; and receiving a periphery of the cassette into the cassette receiver based on an alignment between the periphery of the cassette and the cassette receiver, wherein the alignment is guided by the pre-alignment feature, wherein the pre-alignment feature comprises a support shelf, including multiple shelf components, extending in a longitudinal direction and defining a plurality of slots spaced from each other in the longitudinal direction, the plurality of slots extending vertically to a receiving space from the lower portion, wherein the support shelf is configured with a surface to support at least a portion of the cassette as the cassette receiver receives at least one of the bottom portion and the top portion of the cassette, wherein the surface is configured to retain the lower portion of the cassette.

* * * * *